United States Patent [19]
Hamley et al.

[11] Patent Number: 6,063,789
[45] Date of Patent: May 16, 2000

[54] AMINOISOQUINOLINES AND AMINOTHEINOPYRIDINE DERIVATIVES AND THEIR USE AS ANTI-INFLAMMATORY AGENTS

[75] Inventors: Peter R Hamley, Rothley; James E MacDonald, Pittsford, both of United Kingdom; James R Matz, Fairport, N.Y.; Alan C Tinker, Loughborough, United Kingdom

[73] Assignee: Astra Pharmaceuticals, Ltd., London, United Kingdom

[21] Appl. No.: 08/894,448

[22] PCT Filed: Apr. 9, 1997

[86] PCT No.: PCT/SE97/00589

§ 371 Date: Aug. 19, 1997

§ 102(e) Date: Aug. 19, 1997

[87] PCT Pub. No.: WO97/38977

PCT Pub. Date: Oct. 23, 1997

[30] Foreign Application Priority Data

Apr. 13, 1996 [GB] United Kingdom ............ 9607717
Apr. 26, 1996 [GB] United Kingdom ............ 9608678
May 24, 1996 [GB] United Kingdom ............ 9610892

[51] Int. Cl.[7] ............ A61K 31/47; A61K 31/435; C07D 471/02; C07D 217/00
[52] U.S. Cl. ............ 514/301; 514/310; 546/114; 546/143
[58] Field of Search ............ 514/301, 310; 546/114, 143

[56] References Cited

U.S. PATENT DOCUMENTS 3,903,095  9/1975  Shen ............ 260/294.8
4,127,720  11/1978  Juby ............ 544/252

FOREIGN PATENT DOCUMENTS 2318399    10/1973  Germany.
1 252 704  11/1971  United Kingdom.
1252704 A  11/1971  United Kingdom.
WO 95/11231 4/1995  WIPO.

OTHER PUBLICATIONS

Chemical Abstracts, vol. 58, p. 503d (= Yakugaku, Z., vol. 82, pp. 352–355 (1962)).
Carpenter et al., "The Isopropyl Cresols," J. Org. Chem., vol. 20, pp. 401–411 (1955).
Chemical Abstracts, vol. 118, 263508j (1993) (= JP 04 348 326 A).
Carroll et al, "Novel Ring–Chain Tautomers Derived from (o–Formylphenyl)ethylamines," J. Org. Chem., vol. 56, pp. 4208–4213 (1991).
Sindelar et al, Potential Antidepressants ..., J. Heterocyclic Chem., vol. 26, pp. 1325–1330 (1989).
Eckert–Maksić etal, "A Theoretical Study of the Additivity of Proton ...," Chem. Eur. J., vol. 2, No. 10, pp. 1251–1257 (1996).
J. Med. Chem., vol. 20, pp. 449–452 (1977).*
Chemical Abstracts, vol. 83, 178766f (= An. Quim., vol. 20, pp. 980–985 (1974)).*
Chemical Astracts, vol. 83, No. 21, Nov. 24, 1975 Columbus, Ohio, US: abstract No. 178755f, XP002023559 *abstract* & AN.QUIM., vol. 70, No. 12, 1974, pp. 980–985, V. Gomez–Parra et al: "Synthesis of heterocyclic combinations using nitrile salts. xiii 1–amino–3,4–dihdrosoquinoline derivatives".
Journal of Medicinal Chemistry, vol. 20, No. 3, Mar. 1977, Washington US, pp. 649–652, XP002023558 Guy D. Diana et al: "Synthesis and antihypertensive activity of 1–amino–3,4–dihydroisoquinolines" *p. 650, compound 9*.
Chemical Abstracts 126:47222, abstract of WO 9633195, Tanaka, 1996.
Chemical Abstracts 122:31544, abstract of WO 9410118, Boyd, 1994.
Chemical Abstracts 78:147822, abstract of nauta, DE 2243789, 1973.

*Primary Examiner*—D. Margaret Seaman
*Attorney, Agent, or Firm*—Nixon & Vanderhye

[57] ABSTRACT

Compounds of formula I

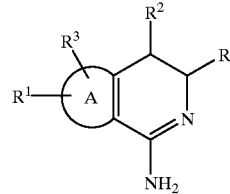

wherein R, $R^1$, $R^2$, and $R^3$ and A are as defined herein, together with pharmaceutically acceptable salts, enantiomers or tautomers are useful as pharmaceuticals, particularly in the treatment of inflammatory disease.

16 Claims, No Drawings

AMINOISOQUINOLINES AND AMINOTHEINOPYRIDINE DERIVATIVES AND THEIR USE AS ANTI-INFLAMMATORY AGENTS

The present invention relates to novel compounds which are aminopyridine derivatives. The invention also concerns related aspects including processes for the preparation of the compounds, compositions containing them and their use as pharmaceuticals. There are also provided chemical intermediates useful for the production of the compounds.

U.S. Pat. No. 4,127,720 discloses 1-amino-3,4-dihydroisoquinolines of the following formula:

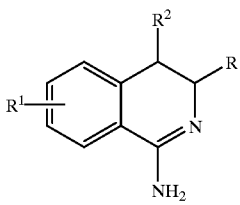

wherein R represents hydrogen, alkyl C1 to 6, or phenyl; $R^1$ represents hydrogen, alkyl C1 to 6, alkoxy C1 to 6 or halogen; and $R^2$ represents hydrogen, alkyl C1 to 6 or unsubstituted phenyl.

U.S. Pat. No. 4,127,720 discloses the use of these compounds as starting materials for the synthesis of other compounds. There is no disclosure of pharmaceutical use. Specifically mentioned compounds are: 1-amino-3,4-dihydro-7-methoxyisoquinoline, 1-amino-3,4-dihydro-6-methoxyisoquinoline and (±)-1-amino-4-ethyl-3,4-dihydroisoquinoline.

"Synthesis and antihypertensive activity of 1-amino-3,4-dihydroisoquinolines", G D Diana et al, J Med. Chem., vol 20, No 3, March 1977, pp 449 to 452 discloses that the hydroiodide salt of 1-amino-3,4-dihydroisoquinoline has antihypertensive activity.

WO 95/11231 discloses a decahydroisoquinoline as a nitric oxide synthase (NOS) inhibitor.

"Synthesis of heterocyclic combinations using nitrile salts. XIII. 1-amino-3,4-dihydroisoquinoline derivatives", V Gomez-Parra et al, An. Quim., vol 70, No 12, 1974, pp 980 to 985 discloses 1-amino-3,4-dihydroisoquinoline derivatives in which the amino group is substituted.

"Bischler-Napieralski reaction of N(3,4-dimethoxyphenylethyl)urea", T Yamazaki et al, Yakugaku Zasshi, vol 82, 1962, pp 352 to 355 discloses 1-amino-6,7-dimethoxy-3,4-dihydroisoquinoline.

According to the invention, there is provided a compound of formula I

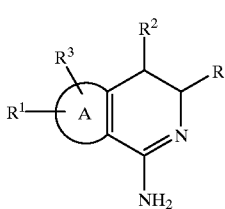

wherein:
R represents
(i) phenyl, benzothiazolyl or a six membered heterocyclic aromatic ring containing 1 to 3 nitrogen atoms, which phenyl, benzo ring of the benzothiazolyl or heterocyclic aromatic ring is optionally substituted by alkyl C1 to 6, alkoxy C1 to 6, halogen, hydroxy, thioalkyl C1 to 6, benzyloxy, or a group —Q(CH$_2$)$_p$NR$^4$R$^5$; or (ii) alkyl C1 to 8, cycloalkyl C3 to 8, alkynyl C2 to 8, piperidyl, phenylalkyl C7 to 14, which alkyl, cycloalkyl, alkynyl, or piperidyl is optionally substituted by a group —(CH$_2$)$_p$NR$^4$R$^5$, the phenylalkyl being optionally substituted by a group —(CH$_2$)$_p$NR$^4$R$^5$, alkyl C1 to 6, alkoxy C1 to 6, halogen or nitro; or (iii) a 5 membered heterocyclic aromatic ring containing 1 to 3 heteroatoms selected from O, N or S, optionally substituted by alkyl C1 to 6, phenylalkyl C7 to 14 or halogen; or (iv) hydrogen or phenylalkynyl C7 to 14;

Q represents O, NR$^6$ or a bond;

$R^1$ represents hydrogen, alkyl C1 to 6, alkoxy C1 to 6, trimethylsilyl or halogen;

$R^2$ represents hydrogen, alkyl C1 to 6 or phenyl optionally substituted by alkyl C1 to 6, alkoxy C1 to 6, halogen or hydroxy;

$R^3$ represents hydrogen or halogen;

$R^4$, $R^5$ and $R^6$ independently represent hydrogen or alkyl C1 to 6, or —NR$^4$R$^5$ together represents piperidyl, pyrrolidinyl or morpholinyl;

p represents an integer 1 to 5; and

A represents a thieno or benzo ring;

provided that when A represents a benzo ring and Q represents O, p does not represent 1; or a pharmaceutically acceptable salt, enantiomer or tautomer thereof;

provided that when A represents a benzo ring, compounds of formula I in which R represents hydrogen, alkyl C1 to 6 or phenyl, $R^1$ represents hydrogen, alkyl C1 to 6, alkoxy C1 to 6 or halogen, $R^2$ represents hydrogen, alkyl C1 to 6 or unsubstituted phenyl and R represents hydrogen are excluded.

The invention further provides a process for the preparation of these compounds or pharmaceutically acceptable salts, enantiomers or tautomers thereof.

According to the invention, there is also provided a compound of formula I, or a pharmaceutically acceptable salt, enantiomer or tautomer thereof, for use as a pharmaceutical, provided that the hydroiodide salt of the compound of formula I in which A represents a benzo ring and each of R, $R^1$, $R^2$ and $R^3$ represents hydrogen, for use as a pharmaceutical is excluded.

Another aspect of the invention provides the use of a compound of formula I or a pharmaceutically acceptable salt, enantiomer or tautomer thereof, in the manufacture of a medicament, for the treatment or prophylaxis of inflammatory disease.

According to the invention, there is also provided a method of treating, or reducing the risk of, inflammatory disease in a patient suffering from, or at risk of, said disease, wherein the method comprises administering to the patient a compound of formula I or a pharmaceutically acceptable salt, enantiomer or tautomer thereof.

Preferably, when A represents a thieno ring the compound is a thieno[2,3-c]pyridine or a thieno[3,2-c]pyridine compound of formula I.

In one embodiment, R represents 2-benzothiazolyl, ethynyl, cyclopropyl, fluorophenyl (eg, 2-, 3- or 4-fluorophenyl), benzyloxyphenyl (eg, 4-benzyloxyphenyl), thiomethylphenyl (eg, 4-thiomethyl), methylphenyl (eg, 2-, 3- or 4-methylphenyl), methoxyphenyl (eg, 4-methoxyphenyl), chlorophenyl (eg, 2-, 3- or 4-chlorophenyl), furyl (eg, 2- or 3-furyl), thienyl (eg, 2- or 3-thienyl), pyridyl (eg, 3- or 4-pyridyl), phenylethynyl, amionopropyloxyphenyl (eg, 4-(3-aminopropyloxy) phenyl), aminoethylphenyl (eg, 3-(2-aminoethyl)phenyl or 4-(2-aminoethyl)phenyl), aminopropylphenyl (eg, 3-(3-aminopropyl)phenyl), thiazolyl (eg, 2-thiazolyl), imidazolyl (eg, 2-imidazolyl), methyl, ((dimethylamino)methyl)phenyl (eg, 2- or 3-((dimethylamino)methyl)phenyl), propynyl (eg, 1-propynyl), butylethynyl (eg, tert-butylethynyl), phenylethynyl, benzylpyrrolyl (eg, 1-benzyl-2-pyrrolyl), methylpyrrolyl (eg, 1-methyl-2-pyrrolyl), ethyl, cyclobutyl, hydroxyphenyl ( eg, 4-hydroxyphenyl) or propyl.

The process mentioned above, for the preparation of compounds of the invention, or pharmaceutically acceptable salts, enantiomers or tautomers thereof comprises:

(a) hydrolysis and/or deprotection of a compound of formula II or a protected derivative thereof, or hydrolysis and/or deprotection of a pharmaceutically acceptable salt, enantiomer or tautomer of a compound of formula II or said protected derivative, wherein formula II is

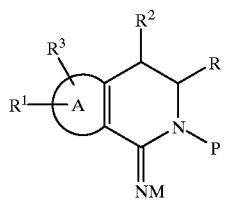

II

A, R, $R^1$, $R^2$ and $R^3$ being as defined above, P representing a protecting group and M representing an alkaline metal; or (b) deprotection of a compound of formula IIIa or IIIb or of a pharmaceutically acceptable salt, enantiomer or tautomer thereof

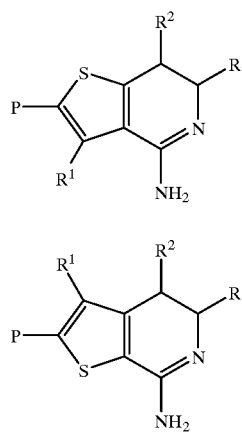

IIIa

IIIb wherein R, $R^1$ and $R^2$ are as defined above and P represents a protecting group; or (c) treating a compound of formula IV or a pharmaceutically acceptable salt, enantiomer or tautomer thereof with ammonia, wherein formula IV is

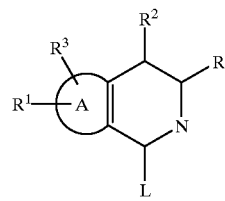

IV wherein A, R, $R^1$, $R^2$ and $R^3$ are as defined above and L is a leaving group; or (d) preparation of a compound of formula I in which R represents ethynyl, or of a pharmaceutically acceptable salt, enantiomer or tautomer of such a compound, by hydrolysis of a corresponding compound in which R represents trimethylsilylethynyl; or (e) reaction of a compound of formula V or a pharmaceutically acceptable salt, enantiomer or tautomer thereof, wherein formula V is

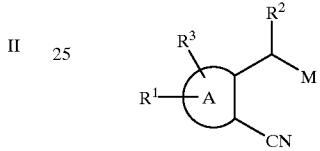

V wherein A, $R^1$, $R^2$ and $R^3$ are as defined above and M represents an alkaline metal, with a compound of formula VI or a pharmaceutically acceptable salt, enantiomer or tautomer thereof, wherein formula VI is

VI wherein R is as defined above; or (f) preparation of a compound or a pharmaceutically acceptable salt, enantiomer or tautomer thereof, wherein the compound is of formula I in which R represents alkyl C1 to 8 substituted by a group —$(CH_2)_p NR^4 R^5$ and one or both of $R^4$ and $R^5$ represents alkyl C1 to 6, by alkylating a corresponding compound in which one or more of $R^4$ and $R^5$ represents hydrogen; or (g) preparation of a compound or a pharmaceutically acceptable salt, enantiomer or tautomer thereof, wherein the compound is of formula I in which R represents phenyl or a six membered heterocyclic aromatic ring, the phenyl or heterocyclic aromatic ring being substituted by a group —$Q(CH_2)_p NR^4 R^5$ and one or both of $R^4$ and $R^5$ represents alkyl C1 to 6, by alkylating a corresponding compound in which one or more of $R^4$ and $R^5$ represents hydrogen; or (h) deprotection of a compound of formula I, or a pharmaceutically acceptable salt, enantiomer or tautomer thereof, in which one or both nitrogen atoms and/or another atom is protected; or (i) preparation of a compound or a pharmaceutically acceptable salt, enantiomer or tautomer thereof, wherein the compound is of formula I in which R represents phenyl or a six membered heterocyclic aromatic ring substituted by a group —$Q(CH_2)_p NH_2$, by reduction of the corresponding azide; or (j) preparation of a compound or a pharmaceutically acceptable salt, enantiomer or tautomer thereof, wherein the compound is of formula I in which R represents piperidyl, by reduction of a corresponding compound in which R represents pyridyl.

In process (a), the hydrolysis step may be performed by methods well known in the art. For example, the compound of formula II may be treated with aqueous acid, e.g. dilute hydrochloric acid. Alkaline metals M include lithium, magnesium, sodium and potassium.

In processes (a) and (b), suitable protecting groups P include alkyl, aralkyl, acyl, acyl sulphonyl, aryl sulphonyl and trialkylsilyl. We prefer that P represents trialkylsilyl especially trimethylsilyl. When P represents trialkylsilyl, the protecting group may be removed by hydrolysis e.g. with tetra-n-butylammonium fluoride. When P represents alkyl, aralkyl, acyl, acyl sulphonyl or aryl sulphonyl, the protecting group may be removed by reduction e.g. using zinc in acetic acid. Further details of processes for the removal of these protecting groups may be found by reference to the standard text "Protecting groups in Organic Synthesis", 2nd Edition (1991) by Greene and Wuts.

In process (c), the reaction may be performed by combining the reactants in a polar protic solvent, e.g. methanol, ethanol or propanol at a temperature between room temperature and the boiling temperature of the solvent for a period of 1 to 12 hours, or until reaction is complete. We prefer, although it is not required, that the reaction be performed in the presence of an ammonium salt e.g. ammonium iodide. Further details of this process may be obtained by reference to Gomez-Parra et al. (1974) An. Quim. 70, 980–985. Suitable leaving groups L include thioalkyl, sulphonic acid, trifluorocarbon sulphonic acid, halide, alkyl and aryl alcohols and tosyl groups; others are recited in 'Advanced Organic Chemistry', J. March (1985) 3rd Edition, McGraw-Hill on page 315 and are well known in the art.

In process (d), the hydrolysis will preferably be carried out in the presence of base, in a polar protic solvent, typically over a period of up to 120 hours.

In process (e), the reaction may be performed in an inert solvent, for example THF, at low temperature, typically between −78° C. and room temperature. It is preferred, although it is not required, to perform the reaction in the presence of at least one equivalent of a polar additive such as hexamethylphosphoric triamide (HMPA) or 1,3-dimethyl-3,4,5,6-tetrahydro-2(1H)-pyrimidone (also known as dimethylpropyleneurea, DMPU).

In processes (f) and (g), the aklylation reaction may be performed by processes well known in the art. For example, the amine may be reacted with an alkyl halide, especially the bromide or iodide.

In process (h), protecting groups for amines are described in process (a) above. Alcohol groups may be protected, for example, by treatment with an enol ether e.g. dihydropyran, which protecting group is removable by subsequent treatment with dilute acid. Other protecting groups and further details of processes for their removal may be found by reference to the standard text "Protecting groups in Organic Synthesis", 2nd Edition (1991) by Greene and Wuts. We prefer to protect the reactive positions of heterocycles with a trimethylsilyl protecting group, which group may typically be removed by treatment with tetra-n-butylammonium fluoride.

In process (i), the reduction may be performed by treatment with tin(II) chloride. The corresponding azide derivatives may be prepared by processes analogous to those used for the preparation of compound of formula I.

In process (j), the reduction reaction may be performed by hydrogenating the corresponding pyridyl derivative over platinum oxide or Pd/C.

Salts of compounds of formula I may be formed by reacting the free base or a salt, enantiomer, tautomer or protected derivative thereof, with one or more equivalents of the appropriate acid. The reaction may be carried out in a solvent or medium in which the salt is insoluble or in a solvent in which the salt is soluble, e.g. water, dioxane, ethanol, tetrahydrofuran or diethyl ether, or a mixture of solvents, which may be removed in vacuo or by freeze drying. The reaction may be a metathetical process or it may be carried out on an ion exchange resin.

Compounds of formula II may be prepared by cyclising a compound of formula VII

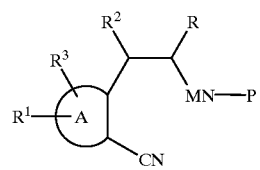

VII wherein A, R, $R^1$, $R^2$, $R^3$ M and P are as defined above.

The cyclisation reaction will generally be performed by warming the compound of formula VII in an inert solvent for up to 4 hours. We have found that the temperature and duration of the reaction will depend greatly on the nature of protecting group P and in some cases, the reaction may proceed between −78° C. and room temperature with little or no heating being required at all. The reaction may be accelerated, or lower temperatures may be used, by performing the reaction in the presence of acid.

Compounds of formula VII may be prepared by reaction of compounds of formula V and VI. However, compounds of formula VII may not be isolable and ring closure may take place to produce a compound of formula II directly.

Compounds of formula IIIa or IIIb may be prepared by processes analogous to those described above for the preparation of compounds of formula I.

Compounds of formula IV may be prepared by methods generally known, for example by reference to Lora-Tamayo et al. (1966) Tetrahedron 8 (Suppl.), 305–312; Gittos et al. (1976) J. Chem. Soc. Perkin Trans. 1, 33–38 and Diana et al. (1977) J. Med. Chem. 3, 449–451. These methods include the formation of thioalkyl derivatives of formula IV by cyclisation of an isothiocyanate and the formation of an iminoester derivative of formula IV by treatment of the corresponding cyclic amide with Meerwein reagent (triethyloxonium tetrafluoroborate). These isothiocyanate and iminoester precursors may be readily prepared by methods also disclosed in these papers, or in-references therein, or by conventional methods known per se.

Alternatively, compounds of formula IV in which L represents thioalkyl may be prepared by treatment of a compound of formula VIII

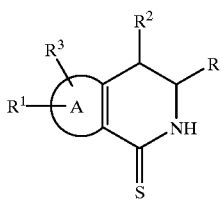

VIII wherein A, R, $R^1$, $R^2$ and $R^3$ are as defined above,
with an alkylating agent such as an alkyl tosylate, methosulphate, mesylate, fluorosulphonate, or halide, especially an alkyl iodide. Suitable solvent for the alkylation reaction include ethers, preferably diethyl ether, tetrahydrofuran, dioxane, lower ketones, e.g. acetone or 2-butanone, halohydrocarbons e.g. dichloromethane and lower alkanols, e.g. methanol. Methyl iodide as the alkylating agent in acetone is particularly suitable. Generally, equimolar to a large excess of the alkylating agent will be used, an amount depending inter alia on the reactivity of the compound of formula VIII and the solubility of reactants in the solvent employed. The alkylation reaction may be carried out at temperatures ranging from ambient to reflux, or in an appropriate sealed vessel at higher temperature.

Compounds of formula VIII may be prepared by ring closure a corresponding compound of formula IX

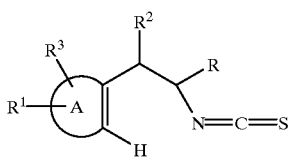

IX wherein A, R, $R^1$, $R^2$ and $R^3$ are as defined above.

This reaction may be performed using conditions analogous to those described for the phenyl analogue compounds in the paper Gittos et al. (1976) mentioned above.

Compounds of formula VIII may also be prepared from a compound of formula X

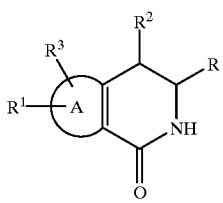

X wherein A, R, $R^1$, $R^2$ and $R^3$ are as defined above,
by treatment with $P_2S_5$ or Lawesson's reagent.

Conditions for this reaction, and details of alternative sulphur containing reagents may be obtained by reference to the paper Smith et al. (1994) J. Org. Chem., 59, 348–354.

Other compounds of formula IV are either known or may be prepared by known methods.

Compounds of formula V in which M represents Li may be prepared by treatment of the corresponding compound of formula V in which M represents hydrogen with a compound of formula XI

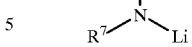

XI wherein $R^7$ represents alkyl or trialkylsilyl. Compounds of formula V in which M represents a metal other than Li may be prepared by analogous methods.

This reaction may be performed in an inert solvent, for example THF, at low temperature, typically below −50° C.

The compounds of formula V in which M represents hydrogen are either known or may be prepared by conventional methods known per se.

Compounds of formula VI may be prepared by treatment of a compound of formula XII

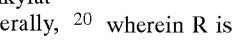
R—CHO         XII wherein R is as defined above,
with ammonia under standard conditions well known in the art.

A protected derivative of a compound of formula VI is obtained by treatment of a compound of formula XII, as defined above,
with a compound of formula XIII

P—$NH_2$         XIII wherein P is as defined above
or a compound of formula XIV

$P_2$N—M         XIV wherein P and M are as defined above.

The reaction of a compound of formula XII with a compound of formula XIII may be performed by combining the two reactants in a polar protic solvent at a temperature between room temperature and the boiling temperature of the solvent and is well known in the art.

The reaction of a compound of formula XII with a compound of formula XIV may be performed by combining the two reactants in an aprotic solvent e.g. THF at low temperature, typically between −10° C. and room temperature, and is well known in the art.

Compounds of formula IX, X, XI, XII, XIII and XIV are either known or may be prepared by conventional methods known per se.

It will be apparent to a person skilled in the art that it may be desirable to protect an amine or other reactive group in an intermediate compound using a protecting group as described in process (f) above.

The following chemical intermediates are useful for producing compounds of the invention, or pharmaceutically acceptable salts, enantiomers or tautomers thereof:
3-methoxy-2-methylbenzonitrile; or
3-fluoro-2-methylbenzonitrile; or
2-fluoro-6-methylbenzonitrile, or
3,6-difluoro-2-methylbenzonitrile; or
4-fluoro-2-methylbenzonitrile; or
3-fluoro-6-methyl-2-trimethylsilylbenzonitrile; or
4-(3-azidopropyloxy)benzaldehyde; or
3-(2-azidoethyl)benzaldehyde; or
3-(3-azidopropyl)benzaldehyde; or
4-(2-azidoethyl)benzaldehyde; or
2-(N,N-dimethyl)aminomethylbenzaldehyde; or
3-(N,N-dimethyl)aminomethylbenzaldehyde; or
4-tert-butyldiphenylsilyloxybenzaldehyde; or 2-cyano-3-methyl-5-trimethylsilylthiophene; or
3-cyano-2-methyl-5-trimethylsilylthiophene; or
5-(trimethylsilyl)thiazole-2-carboxaldehyde; or
1-amino-3-(4-(3-azidopropyloxy)phenyl)-3,4-dihydroisoquinoline; or
1-amino-3-(3-(2-azidoethyl))phenyl-3,4-dihydroisoquinoline; or
1-amino-3-(4-(2-aminoethyl)phenyl)-3,4-dihydroisoquinoline; or
1-amino-3-(3-(3-azidopropyl)phenyl)-3,4-dihydroisoquinoline; or
4-methylthio-6,7-dihydrothieno[3,2-c]pyridine.

The compounds of formula I may exist in enantiomeric forms. Therefore, all enantiomers, diastereomers, racemates and mixtures thereof are included within the scope of the invention. The various optical isomers may be isolated by separation of a racemic mixture of the compounds using conventional techniques, e.g. fractional crystallisation, or HPLC. Alternatively the individual enantiomers may be made by reaction of the appropriate optically active starting materials under reaction conditions which will not cause racemisation.

Compounds of formula II, III, IV, V, VI, VII, VIII, IX, X and XII and other intermediates may also exist in enantiomeric forms and may be used as purified enantiomers, diastereomers, racemates or mixtures.

The compounds of formula I may exist in the alternative tautomeric form IA

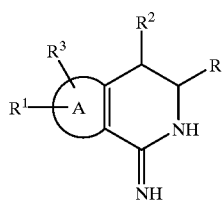

IA wherein A, R, $R^1$, $R^2$ and $R^3$ are as defined above. Compounds of formula I may be provided in either tautomeric form or as a mixture thereof.

Compounds of formula IIIa or IIIb may also exist in an alternative tautomeric form IIIa' or IIIb' respectively

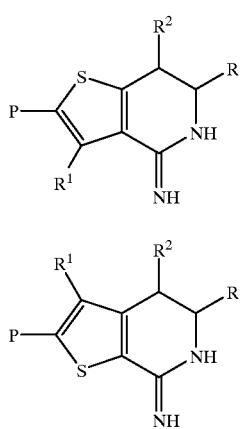

IIIa'

IIIb' wherein A, R, $R^1$ and $R^2$ are as defined above.

"Alkyl", including in for example "thioalkyl" and "phenylalkyl", includes straight chain or branched alkyl groups. "Alkoxy" and "alkynyl" are to be interpreted similarly.

The compounds of formula I, and pharmaceutically acceptable salts, enantiomers and tautomers thereof, are useful because they possess pharmacological activity in animals. In particular, the compounds are active as inhibitors of the inducible isoform of the enzyme nitric oxide synthase (NOS) present in macrophages and as such are expected to be useful as therapy, eg as anti-inflammatory agents.

The compounds and their pharmaceutically acceptable salts, enantiomers and tautomers are indicated for use in the treatment or prophylaxis of diseases or conditions in which synthesis or oversynthesis of nitric oxide synthase forms a contributory part. In particular, the compounds are indicated for use in the treatment of inflammatory conditions in mammals including man.

Conditions that may be specifically mentioned are:
osteoarthritis, rheumatoid arthritis, rheumatoid spondylitis, gouty arthritis and other arthritic conditions, inflamed joints;
eczema, psoriasis, dermatitis or other inflammatory skin conditions such as sunburn;
inflammatory eye conditions including uveitis and conjunctivitis;
lung disorders in which inflammation is involved, e.g. asthma, bronchitis, pigeon fancier's disease, farmer's lung, acute respiratory distress syndrome, bacteraemia, endotoxaemia (septic shock) and pancreatitis;
conditions of the gastrointestinal tract including aphthous ulcers, gingivitis, Crohn's disease (a condition of the small and sometimes also of the large intestine), atrophic gastritis and gastritis varialoforme (conditions of the stomach), ulcerative colitis (a condition of the large and sometimes of the small intestine), coeliac disease (a condition of the small intestine), regional ileitis (a regional inflammatory condition of the terminal ileum), peptic ulceration (a condition of the stomach and duodenum) and irritable bowel syndrome; pyresis; pain; damage to the gastrointestinal tract resulting from infections by, for example, *Helicobacter pylori*, or treatments with non-steroidal anti-inflammatory drugs; and other conditions associated with inflammation.

The compounds of formula I may also be useful in the treatment of diseases or conditions besides those mentioned above. For example, the compounds of formula I may be useful in the treatment of hypotension associated with septic and/or toxic shock, in the treatment of dysfunction of the immune system, as an adjuvant to short-term immunosuppression in organ transplant therapy, in the treatment of vascular complications associated with diabetes and in co-therapy with cytokines, e.g. TNF or interleukins.

The compounds of formula I may also show inhibitory activity against the neuronal isoform of nitric oxide synthetase. Thus they may also be useful in the treatment of hypoxia, e.g. in cases of cardiac arrest and stroke, neurodegenerative disorders including nerve degeneration and/or nerve necrosis in disorders such as hypoxia, hypoglycaemia, epilepsy, and in external wounds (such as spinal cord and head injury), hyperbaric oxygen convulsions and toxicity, dementia e.g. pre-senile dementia, Alzheimer's disease and AIDS-related dementia, Sydenham's chorea, Parkinson's disease, Tourette's Syndrome, Huntington's disease, Amyotrophic Lateral Sclerosis, Korsakoff's disease, imbecility relating to a cerebral vessel disorder, sleeping disorders, schizophrenia, depression, autism, seasonal affective disorder, jet-lag, depression or other symptoms associated with Premenstrual Syndrome (PMS), anxiety and septic shock. Compounds of formula I may also be expected to show activity in the prevention and reversal of tolerance to opiates and diazepines, treatment of drug addiction, relief of pain and treatment of migraine and other vascular headaches, neurogenic inflammation, in the treatment of gastrointestinal motility disorders, cancer and in the induction of labour.

For the above mentioned therapeutic indications, the dosage administered will, of course, vary with the compound employed, the mode of administration and the treatment desired. However, in general, satisfactory results are obtained when the compounds are administered at a daily dosage of the solid form of between 1 mg and 2000 mg per day.

The compounds of formula I, and pharmaceutically acceptable derivatives thereof, may be used on their own, or as a pharmaceutical composition in which the compound or derivative is in admixture with a pharmaceutically acceptable adjuvant, diluent or carrier. For example in a form appropriate for enteral or parenteral administration. The pharmaceutical composition preferably comprises less than 80% and more preferably less than 50% of the compound or derivative. Examples of suitable adjuvants, diluents and carriers are well known to a person skilled in the art.

The compounds of formula I and their pharmaceutically acceptable salts, enantiomers and tautomers have the advantage that they are less toxic, more efficacious, are longer acting, have a broader range of activity, are more potent, are more selective, produce fewer side effects, are more easily absorbed or have other useful pharmacological properties, than compounds of similar structure.

The invention is illustrated, but in no way limited by, the examples below. The preparation of intermediates for the production of the examples is as follows.
Preparation of Intermediates

EXAMPLE A
Methoxy-2-methylbenzonitrile

Hydroxylamine hydrochloride (0.75 g, 11 mmol) was added to 3-methoxy-2-methylbenzaldehyde (1.25 g, 8.32 mmol) in formic acid (89–91%) (10 ml), and the mixture heated to reflux for 40 min., cooled, diluted with ice-cold water, basified with 10% aqueous sodium hydroxide solution and extracted with diethyl ether. The organic extract was washed with saturated aqueous sodium chloride (50 ml), dried over magnesium sulphate and evaporated. The residue was purified by flash chromatography over silica gel eluting with 5% diethyl ether in hexane to afford the product as a white solid (0.98 g). $M^+$ 147; 360 MHz $^1$H n.m.r (CDCl$_3$) 7.26–7.17 (2H, m), 7.02 (1H, d, J 7.9 Hz), 3.86 (3H, s), 2.41 (3H, s).

EXAMPLE B

Following the method of Example A, the following compound was prepared:
3-Fluoro-2-methylbenzonitrile. $M^+$ 135; 360 MHz $^1$H n.m.r (CDCl$_3$) 7.49–7.39 (1H, m), 7.28–7.17 (2H, m), 2.47 (3H, s).

EXAMPLE C
2-Fluoro-6-methylbenzonitrile n-Butyllithium (1.45M, 44.0 mmol, 30.3 ml) was added dropwise to a stirred solution of tetramethyleneethylenediamine (48 mmol, 6.2 ml) in tetrahydrofuran (THF) at −22° C. After 15 min., a further portion of n-butyllithium (120 mmol, 82.8 ml) was added dropwise, and after a further 15 min. 2-Fluorobenzaldehyde (40.0 mmol. 4.21 ml) in THF (16 ml) was added dropwise. The mixture was stirred at −22° C. for 16 h. Methyl iodide (12.5 ml) was added dropwise and the mixture was warmed to room temperature over 30 min., poured into 2N hydrochloric acid and ice, extracted twice with diethyl ether, dried over magnesium sulphate and evaporated to give a brown oil. This was dissolved in formic acid (50 ml) and treated with hydroxylamine hydrochloride (52 mmol, 3.6 g). The mixture was heated at reflux for 16 h, cooled to room temperature and poured into ice water, basified with 10% aqueous sodium hydroxide, extracted twice with diethyl ether, dried over magnesium sulphate and evaporated. The residue was purified by flash chromatography on silica gel, eluting with dichloromethane, to give a yellow solid (2.50 g). This was further purified by flash chromatography, eluting with 5% diethyl ether/hexane, to furnish the title compound as a white/yellow solid (1.95 g). $M^+$ 135; 360 MHz $^1$H n.m.r (CDCl$_3$) 7.45 (1H, dt, J 5.9, 8.1 Hz), 7.11 (1H, d, J 7.8 Hz), 7.03 (1H, t, J 8.6 Hz), 2.56 (3H, s).

EXAMPLE D
3,6-Difluoro-2-methylbenzonitrile

This was prepared from 2,5-difluorobenzaldehyde by the method of Example C, with slight modification to the first step: after the addition of the aldehyde, the mixture was stirred for 15 min., cooled to −45° C., stirred for 3 h, methyl iodide added and the reaction worked-up as before. Subsequent reaction gave the title compound as a yellow oil. $M^+$ 153; 360 MHz $^1$H n.m.r (CDCl$_3$) 7.25 (1H, dt, J 8.8, 4.6 Hz), 7.02 (1H, dt, J 8.6, 3.9 Hz), 2.48 (3H, d, J 2.3 Hz).

EXAMPLE E
4-Fluoro-2-methylbenzonitrile

This was prepared from 4-fluorobenzaldehyde by the method of Example C, with slight modification to the first step: the reaction was conducted at −78° C. until the second addition of n-butyllithium was complete. The reaction was then warmed to −20° C. and stirred for 2 h, cooled to −45° C. and quenched with methyl iodide as before. Subsequent reaction gave the title compound as a pale yellow solid. $M^+$ 135; 360 MHz $^1$H n.m.r (d$_6$-DMSO) 7.61 (1H, dd, J 5.5, 8.5 Hz), 7.05–6.96 (2H, m), 2.56 (3H, s).

EXAMPLE F
3-Fluoro-6-methyl-2-trimethylsilylbenzonitrile n-Butyllithium (1.40M in hexanes, 11.8 mmol, 8.44 ml) was added dropwise to a stirred solution of diisopropylamine (1.84 ml) in THF (5 ml) at 0° C. After 30 min., the solution was cooled to −78° C. and 3-fluoro-6-methylbenzonitrile (1.60 g, 11.8 mmol) in THF (5 ml) was added dropwise. The pale purple anion was stirred for 20 min., trimethylsilylchloride (3.0 ml, 24 mmol) was added and the mixture warmed to room temperature over 1 h, evaporated, the residue taken up in a small amount of diethyl ether and filtered. Evaporation of the filtrate gave an off-white crystalline solid (2.3 g), m.p. 71–73° C.

EXAMPLE G
4-(3-Azidopropyloxy)benzaldehyde
a) 4-(3-Bromopropyloxy)benzaldehyde A solution of 4-hydroxybenzaldehyde (3.7 g, 30 mmol) in DMF (10 ml) was added cautiously to a stirred solution of sodium hydride (60% in oil, 1.44 g) in DMF (80 ml). After 30 min., 1,3-dibromopropane (9.2 ml, 90 mmol) in DMF (10 ml) was added dropwise, the mixture stirred for 16 h, poured into water, extracted twice with ethyl acetate, and the combined extracts washed with water and saturated aqueous sodium chloride, dried over sodium sulphate and evaporated. The residue was purified by flash chromatography on silica, eluting with 25% diethyl ether in hexane, to afford 4-(3-bromopropyloxy)benzaldehyde (3.85 g). M⁺ 205; 360 MHz ¹H n.m.r (CDCl₃) 7.85 (2H, d, J 7.0 Hz), 7.01 (2H, d, J 7.0 Hz), 4.20 (2H, t, J 5.8 Hz), 3.62 (2H, t, J 6.4 Hz), 2.36 (2H, pentet, J 6.1 Hz).

b) 4-(3-Azidopropyloxy)benzaldehyde

A mixture of 4-(3-bromopropyloxy)benzaldehyde (3.5 g, 14.5 mmol) and sodium azide (29 mmol, 1.9 g) in DMSO (70 ml) was stirred for 16 h, poured into water (100 ml) and extracted twice with diethyl ether. The extracts were washed with water (50 ml) and saturated aqueous sodium chloride, dried over sodium sulphate and evaporated to give a colourless oil (2.75 g). M⁺ 205; 360 MHz ¹H n.m.r (CDCl₃) 7.84 (2H, d, J 11 Hz), 7.02 (2H, d, J 11 Hz), 4.14 (2H, t, J 5.9 Hz), 3.55 (2 H, t, J 6.5 Hz), 2.09 (2 H, app. pentet, J 6.2 Hz).

EXAMPLE H
3-(2-Azidoethyl)benzaldehyde a) 3-Bromobenzeneethanol

Borane-dimethylsulphide complex (2.0M in THF, 49 ml) was added dropwise to a stirred solution of 3-bromostyrene (10 g, 55 mmol) in THF (130 ml) at 0° C. and the solution was stirred for 3 h at room temperature. 10% Aqueous sodium hydroxide was added cautiously, followed by hydrogen peroxide (30% wt. solution in water, 6 ml) dropwise. After a further 16 h, the mixture was diluted with water, extracted twice with ethyl acetate, the combined extracts washed with saturated sodium bisulphite solution and saturated sodium chloride solution, dried over sodium sulphate and evaporated to give a colourless oil. Purification by flash chromatography, eluting with 30% diethyl ether/hexane gave a colourless oil, [M+Si(CH₃)₃ derivative]⁺ 272.

b) 3-Bromobenzeneethanol 4-methylbenzenesulphonate

4-Methylbenzenesulphonyl chloride (4.38 g) was added portionwise to a solution of 3-bromobenzeneethanol [Example H(a)] (2.30 g, 11.4 mmol) in pyridine (30 ml) at 0° C., and the mixture stood at −20° C. for 16 h. The mixture was diluted with water, extracted with diethyl ether, the extracts combined, washed twice with aqueous 4N hydrochloric acid and once with saturated aqueous sodium chloride, dried over sodium sulphate and evaporated to afford a pale yellow oil (3.98 g). [M-OTs]⁺ 182; 360 MHz ¹H n.m.r (CDCl₃) 7.66 (2H, d, J 8.3 Hz), 7.34 (1H, dm, J 7.9 Hz), 7.30–7.26 (2H, m), 7.20 (1H, d, J 1.5 Hz), 7.12 (1H, t, J 7.7 Hz), 7.05 (1H, d, J 7.7 Hz), 4.20 (2H, t, J 6.8 Hz), 2.91 (2H, t, J 6.8 Hz), 2.44 (3H, s).

c) 1-Azido-2-(3-bromophenyl)ethane

A mixture of 3-bromobenzeneethanol 4-methylbenzenesulphonate [Example H(b)] (3.96 g, 11.2 mmol) and sodium azide (22.4 mmol, 1.46 g) in DMSO (50 ml) was stirred at room temperature for 16 h, diluted with water (200 ml), extracted with diethyl ether (2×40 ml), the combined extracts washed with saturated aqueous sodium chloride (40 ml), dried over sodium sulphate and evaporated, to give the product as a pale yellow oil (2.46 g). M⁺ 227; 360 MHz ¹H n.m.r (CDCl₃) 7.52 (1H, s), 7.45–7.42 (1H, m), 7.31–7.25 (2H, m), 3.58 (2H, t, 7.0 Hz), 2.85 (2H, t, J 7.0 Hz).

d) 3-(2-Azidoethyl)benzaldehyde, n-Butyllithium (1.50M in hexane, 10.8 mmol, 7.23 ml) was added dropwise at −78° C. to a solution of 1-azido-2-(3-bromophenyl)ethane [Example H(c )] (2.45 g, 10.8 mmol) in THF (80 ml). The bright yellow solution was stirred for 20 min., N-formylmorpholine (2.4 ml) in THF (10 ml) was added dropwise, the solution stirred for a further 30 min. and then warmed room temperature over 1 h. The solution was diluted with diethyl ether, washed with saturated aqueous ammonium chloride and saturated aqueous sodium chloride, dried over sodium sulphate and evaporated. The residue was purified by flash chromatography, eluting with 10% diethyl ether/hexane, to furnish the product as a pale yellow oil (750 mg). [M-N₂]⁺ 146; 360 MHz ¹H n.m.r (CDCl₃) 10.02 (1H, s), 7.79–7.76 (2H, m), 7.52–7.50 (2H, m), 3.57 (2H, t, J 7.0 Hz), 2.98 (2H, t, J 7.0 Hz).

EXAMPLE I
3-(3-Azidopropyl)benzaldehyde a) Methyl m-bromocinnamate

Trimethylsilyl chloride (5.6 ml) was added dropwise to a stirred solution of m-bromocinnamic acid (5.0 g, 22 mmol) in methanol (110 ml). After 4 h, the mixture was evaporated to give product as a white solid, M⁺ 242; 360 MHz 1H n.m.r (CDCl₃) 7.67 (1H, s), 7.60 (1H, d, J 16 Hz), 7.50 (1H, d, J 7.9 Hz), 7.43 (1H, d, J 7.9 Hz), 7.26 (1H, d, J 15.6 Hz), 6.43 (1H, d, J 16.1 Hz), 3.81 (3H, s).

b) 3-Bromobenzeneprop-2-enol

Diisobutylaluminium chloride (1.5M in toluene, 85 mmol, 57 ml) was added dropwise to a stirred solution of methyl m-bromocinnamate [Example I(a)] (5.10 g, 21.2 mmol) in toluene (100 ml) at 0° C. The mixture was stirred for 16 h at room temperature, cautiously quenched with 4N hydrochloride acid (100 ml), extracted three times with diethyl ether, the combined extracts dried over sodium sulphate and evaporated to give a pale yellow viscous oil (4.40 g). M⁺ 286; 360 MHz ¹H n.m.r (CDCl₃) 7.58 (1H, s), 7.36 (1H, d, J 7.8 Hz), 7.28 (1H, t, J 7.8 Hz), 7.18 (1H, t, J 7.8 Hz), 6.54 (1H, d, J 15.9 Hz), 6.35 (1H, dt, J 15.9,4 Hz), 4.33 (2H, d, J 4.1 Hz), 2.35 (1H, br.s).

c) 3-Bromobenzenepropanol

A solution of 3-bromobenzeneprop-2-enol [Example I(b)] (4.40 g, 20.8 mmol) in ethanol (100 ml) was stirred for 3 h under 3 atm of hydrogen with 10% palladium on charcoal (5 mol %, 1 g, 1.0 mmol). The mixture was then filtered through celite and the filtrate evaporated. The residue was purified by flash chromatography on silica gel eluting with 20% ethyl acetate/hexane to afford the title compound as a colourless oil (2.10 g), M⁺ 216.

d) 3-Bromobenzenepropanol 4-methylbenzenesulphonate, this was prepared by the method of Example H(b) using 3-bromobenzenepropanol [Example I(c)], [M-OTs]⁺ 198; 360 MHz ¹H n.m.r (CDCl₃) 7.79 (1H, d, J 8.2 Hz), 7.37–6.99 (7H, m), 4.02 (2H, t, J 6.1 Hz), 2.62 (2H, t, J 7.5 Hz), 2.46 (3H, s), 1.98–1.90 (2H, m).

e) 1-Azido-3-(3-bromophenyl)propane, this was prepared by the method of Example H(c) using 3-bromobenzenepropanol 4-methylbenzenesulphonate [Example I(d)] [M-N₂]⁺213; 360 MHz ¹H n.m.r (d₆-DMSO) 7.44 (1H, s), 7.39 (1H, d, J 7.1 Hz), 7.29–7.22 (2H, m), 3.33 (2H, t, J 4.5 Hz), 2.64 (2H, t, J 7.8 Hz), 1.87–1.78 (2H, m).

f) 3-(3-Azidopropyl)benzaldehyde, this was prepared by the method of Example H(d) using 1-azido-3-(3-bromophenyl) propane [Example I(e)] [M-N₂]⁺ 161; 360 MHz ¹H n.m.r (CDCl₃) 10.01 (1H, s), 7.75–7.72 (2H, m), 7.51–7.47 (2H, m), 3.32 (2H, t, J 6.7 Hz), 2.80 (2H, t, J 7.5 Hz), 1.95 (2H, pentet, J 7 Hz).

EXAMPLE J
4-(2-Azidoethyl)benzaldehyde a) 4-Bromobenzeneethanol 4-methylbenzenesulphonate, this was prepared by the method of Example H(b) using 4-bromobenzeneethanol,[M-OTs]⁺ 184/182.

b) 1-Azido-2-(4-bromophenyl)ethane, this was prepared by the method of Example H(c) using 4-bromobenzeneethanol 4-methylbenzenesulphonate [Example J(a)], M⁺ 227; 360 MHz ¹H n.m.r (CDCl₃) 7.50 (2H, d, J 8.2 Hz), 7.25 (2H, d, J 8.2 Hz), 3.56 (2H, t, J 7.0 Hz), 2.83 (2H, t, J 7.0 Hz).

c) 4-(2-Azidoethyl)benzaldehyde, this was prepared by the method of Example H(d) using 1-azido-2-(4-bromophenyl) ethane [Example J(b)], [M-N$_2$]$^+$ 147; 360 MHz $^1$H n.m.r (CDCl$_3$) 10.03 (1H, s), 7.90 (2H, d, J 8.0 Hz), 7.56 (2H, d, J 8.0 Hz), 3.68 (2H, t, J 6.9 Hz), 3.00 (2H, t, J 6.9 Hz).

EXAMPLE K
2-(N,N-Dimethyl)aminomethylbenzaldehyde
a) 2-Bromo-(N,N-dimethyl)benzylamine Dimethylamine (33% w/w in methanol) (25 ml) was added to 2-bromobenzylbromide (7.5 g 30 mmol) at 0° C. in methanol (35 ml), and the solution stirred for 30 min., evaporated, diluted with water and extracted twice with diethyl ether. The combined extracts were dried over sodium sulphate and evaporated to give product as a yellow oil (6.0 g). M$^+$ 215/213; 360 MHz 1H n.m.r (CDCl$_3$) 7.54 (1H, dd, J 1.2, 8.0 Hz), 7.42 (1H, dd, J 1.6, 7.6 Hz), 7.30–7.26 (1H, m), 7.11 (1H, dt, J 1.7, 7.7 Hz), 3.52 (2H, s), 2.30 (6H, s).

b) 2-(N,N-Dimethyl)aminomethylbenzaldehyde, prepared with the intermediate of Example K(a) using the method of Example H (c); 360 MHz $^1$H n.m.r (CDCl$_3$) 10.41 (1H, s), 7.87 (1H, d, J 6.3 Hz), 7.52 (1H, t, J 7.5 Hz), 7.44 –7.15 (2H, m), 3.8–3.7 (3H, s), 2.24 (3H,s).

EXAMPLE L
3-(N,N-Dimethyl)aminomethylbenzaldehyde
a) 3-Cyano-(N,N-dimethyl)benzylamine, prepared using the method of Example K(a); M$^+$ 160; 360 MHz $^1$H n.m.r (CDCl$_3$) 7.63 (1H, s), 7.55 (2H, m), 7.43 (1H, t, J 7.7 Hz), 3.44 (2H, s), 2.24 (6H, s).

b) 3-(N,N-Dimethyl)aminomethylbenzaldehyde

Diisobutylaluminium hydride (1.0M solution in toluene, 20 ml, 20 mmol) was added dropwise to a solution of 3-cyano-(N,N-dimethyl)benzylamine [Example K(a)] (3.20 g, 20 mmol) in toluene (50 ml). The mixture was stirred at room temperature for 2 h., methanol (30 ml) was cautiously added, followed by methanol/water (1:1, 40 ml) and 10% aqueous sodium hydroxide (100 ml). The mixture was extracted twice with diethyl ether, washed with saturated aqueous sodium chloride, dried over sodium sulphate and evaporated to give a yellow oil (3.0 g). M$^+$ 163; 360 MHz $^1$H n.m.r (CDCl$_3$) 10.02 (1H, s), 7.83 (1H, s), 7.79 (1H, d, J 7.6 Hz), 7.60 (1H, d, J 7.5 Hz), 7.49 (1H, t, J 7.5 Hz), 3.50 (2H, ), 2.26 (6H, s).

EXAMPLE M
4-tert-Butyldilphenylsilyloxybenzaldehyde tert-Butyldiphenylsilylchloride (13.3. mmol, 2.5 ml) was added to a stirred solution of 4-hydroxybenzaldehyde (12 mmol, 1.5 g) and DBU (14 mmol, 2.2 ml) in dichloromethane (25 ml). After 5 min., the solution was washed with water, the aqueous layer was further extracted with dichloromethane and the combined organic extracts were washed with 0.5N hydrochloric acid and saturated sodium bicarbonate solution, dried over sodium sulphate and evaporated. The residue was purified by flash chromatography on silica gel eluting with 15% diethyl ether/hexane to yield a white solid (4.0 g). M$^+$ 360; 360 MHz $^1$H n.m.r (CDCl$_3$) 7.73–7.63 (6H, m), 7.47–7.36 (6H, m), 6.85 (2H, d, J 6.5 Hz), 1.11 (9H, s), 9.80 (1H, s).

EXAMPLE N
2-Cyano-3-methyl-5-trimethylsilylthiophene n-Butyllithium (1.45M in hexanes, 51.9 ml) was added dropwise to a stirred solution of diisopropylamine (11.7ml, 83.0 mmol) in dry THF (150 ml) at –5–0° C. and the solution stirred for 30 min. 1,3-Dimethyl-3,4,5,6-tetrahydro-2(1H)-pyrimidinone (DMPU) (13.6 ml, 0.11 mmol) was added, the mixture was cooled to –78° C. and a solution of 2-cyano-3-methylthiophene (9.27 g, 75.4 mmol) in THF (20 ml) added dropwise, followed by trimethylsilylchloride (19.1 ml) after 30 sec. The mixture was warmed to room temperature over 30 min., evaporated, taken up in diethyl ether, the solids filtered off and the filtrate evaporated to afford a yellow oil. This was purified by flash chromatography on untreated neutral alumina, eluting with 1% diethyl ether in hexane, to give 2-cyano-3-methyl-5-trimethylsilylthiophene as a clear oil (6.52 g). M$^+$ 195; 360 MHz 1H n.m.r. (CDCl3) 7.02 (1H, s), 2.43 (3H, s), 0.33 (9H, s).

EXAMPLE O
3-Cyano-2-methyl-5-trimethylsilylthiophene n-Butyllithium (1.4 M in hexanes, 1.3 ml, 1.8 mmol) was added dropwise to a stirred solution of diisopropylamine (0.25 ml) in dry THF (16 ml) at –5–0° C. and the solution stirred for 30 min. The mixture was cooled to –78° C. and a solution of 3-cyanothiophene (0.20 g, 1.8 mmol) in THF (4 ml) added dropwise, followed by methyl iodide (0.23 ml, 0.35 g, 2.5 mmol) after min. The mixture was stirred for 20 min., warmed to room temperature over 30 min. and evaporated. Meanwhile n-butyllithium (1.4 M in hexanes, 1.31 ml) was added dropwise to a stirred solution of diisopropylamine (0.25 ml) in dry THF (16 ml) at –5–0° C. and the solution stirred for 30 min. The mixture was cooled to 78° C. and the crude 3-cyano-2-methylthiophene prepared above was added dropwise in THF (4 ml), followed by trimethylsilylchloride (0.43 ml) after 1 min. The mixture was stirred for 20 min., warmed to room temperature over 30 min. and evaporated to afford a yellow oil. Purification by flash chromatography on untreated neutral alumina, eluting with 5% diethyl ether in hexane, gave 3-cyano-2-methyl-5-trimethylsilylthiophene as a clear oil (0.20 g). M$^+$ 195; 360 MHz $^1$H n.m.r (CDCl$_3$) 7.19 (1H, s), 2.66 (3H, s), 0.31 (9H, s).

EXAMPLE P
5-(Trimethylsilyl)thiazole-2-carboxaldehyde n-Butyllithium (1.50M in hexane, 39 mmol, 22 ml) was added dropwise at –78° C. to a solution of 5-(trimethylsilyl) thiazole (A. Dondoni et al, *J. Org. Chem*, 1988, 53, 1748) (5.2 g, 33 mmol) in THF (40 ml). After 30 min. a solution of N-formylmorpholine (4.57 g) in THF (40 ml) was added dropwise over 15 min. The resulting red solution was stirred a further 30 mi. and then allowed to warm to room temperature , dilute d with 4N hydrochloric acid and extracted three times with ethyl acetate. The combined extracts were washed with saturated aqueous sodium chloride, dried over sodium sulphate and evaporated to leave a brown oil (5.5 g). M$^+$ 185; 360 MHz 1H n.m.r (CDCl$_3$) 9.89 (1H, s), 7.95 (1H, s), 0.24 (9H, s).

Preparation of Products

EXAMPLE 1
1-Amino-3-(2-fluorophenyl)-3,4-dihydroisoquinoline hydrochloride

Lithium hexamethyldisilylazide (1.0 M in THF, 5.0 ml, 5.0 mmol) was added dropwise to a stirred solution of 2-fluorobenzaldehyde (0.53 ml, 5.0 mmol) in dry THF (5 ml) at –10 ° C., and the imine solution allowed to warm to 0° C. over a period of 2 h. Meanwhile, n-butyllithium (1.45 M in hexanes, 5.0 mmol, 3.5 ml) was added dropwise to a stirred solution of diisopropylamine (5.5 mmol, 0.78 ml) in dry THF (8 ml) at –5–0° C. and the solution stirred for 30 min. DMPU (0.91 ml, 5.0 mmol) was added, the mixture was cooled to –78° C. and a solution of 2-methylbenzonitrile (5.0 mmol, 0.59 ml) in THF (4 ml) was added dropwise. The dark red anion was stirred for 30 min., and the freshly prepared imine solution added dropwise. After 40 min., the mixture was warmed to 0° C. over 30 min., quenched with 6N aqueous hydrochloric acid, extracted three times with dichloromethane and the combined extracts dried over sodium sulphate and evaporated to afford a yellow oil. This was purified by flash chromatography on untreated neutral alumina, eluting with 5% methanol in dichloromethane, increasing the gradient to 10% methanol in dichloromethane to give a pale yellow foam (0.49 g). This was recrystallised from dichloromethane/hexane to afford pale yellow crystals of 1-amino-3-(2-fluorophenyl)-3,4-dihydroisoquinoline hydrochloride (0.35 g), m.p. 204–206 ° C.

The compounds of Example 2–47 were prepared using the method of Example 1 using the appropriate nitriles and aldehydes.

EXAMPLE 2
1-Amino-3-phenyl-3,4-dihydroisoquinoline hydrochloride, prepared using 2-methylbenzonitrile and benzaldehyde; m.p. 204–206° C.

EXAMPLE 3
1-Amino-3-(4-(benzyloxy)phenyl)-3,4-dihydroisoquinoline hydrochloride, prepared using 2-methylbenzonitrile and 4-benzyloxybenzaldehyde; m.p. 248–250° C.

EXAMPLE 4
1-Amino-3-(4-(methylthio)phenyl)-3,4-dihydroisoquinoline hydrochloride, prepared using 2-methylbenzonitrile and 4-methylthiobenzaldehyde; colourless glass. $M^+$ 268. Calc. for $C_{16}H_{17}N_2ClS$: C, 63.0; H, 5.6; N, 9.2; Cl, 11.6; S, 10.5%. Found C, 63.0; H, 5.9; N, 9.3; Cl, 12.0; S, 10.2%.

EXAMPLE 5
1-Amino-3-(4-(methyl)phenyl)-3,4-dihydroisoquinoline hydrochloride, prepared using 2-methylbenzonitrile and 4-methylbenzaldehyde; colourless glass. $M^+$ 236. Calc. for $C_{16}H_{17}N_2Cl$: C, 70.45; H, 6.3; N, 10.3; Cl, 13.0%. Found C, 70.6; H, 6.6; N, 10.35; Cl, 13.0%.

EXAMPLE 6
1-Amino-3-(3-(methyl)phenyl)-3,4-dihydroisoquinoline hydrochloride, prepared using 2-methylbenzonitrile and 3-methylbenzaldehyde; colourless foam. $M^+$ 236. Calc. for $C_{16}H_{17}N_2Cl+0.8$ mol $H_2O$: C, 66.95; H, 6.5; N, 9.8; Cl, 12.35%. Found C, 66.6; H, 6.5; N, 9.7; Cl, 11.8%.

EXAMPLE 7
1-Amino-3-(4-(methoxy)phenyl)-3,4-dihydroisoquinoline hydrochloride, prepared using 2-methylbenzonitrile and 4-methoxybenzaldehyde; colourless glass. $M^+$ 252. Calc. for $C_{16}H_{17}N_2Cl$: C, 66.55; H, 5.9; N, 9.7; Cl, 12.3%. Found C, 66.2; H, 6.3; N, 9.8; Cl, 12.3%.

EXAMPLE 8
1-Amino-5-methoxy-3-phenyl-3,4-dihydroisoquinoline hydrochloride, prepared using 3-methoxy-2-methylbenzonitrile and benzaldehyde; m.p. 252–254° C.

EXAMPLE 9
1-Amino-3-(2-(chloro)phenyl)-3,4-dihydroisoquinoline, prepared using 2-methylbenzonitrile and 2-chlorobenzaldehyde; m.p. 166–168° C.

EXAMPLE 10
1-Amino-3-(3-(chloro)pheny)-3,4-dihydroisoquinoline hydrochloride, prepared using 2-methylbenzonitrile and 3-chlorobenzaldehyde; m.p. 179–182° C.

EXAMPLE 11
1-Amino-3-(4-(chloro)phenyl)-3,4-dihydroisoquinoline hydrochloride, prepared using 2-methylbenzonitrile and 4-chlorobenzaldehyde; m.p. 297–299° C.

EXAMPLE 12
1-Amino-5-chloro-3-phenyl-3,4-dihydroisoquinoline hydrochloride, prepared using 3-chloro-2-methylbenzonitrile and benzaldehyde; colourless foam. $M^+$ 256. Calc. for $C_{15}H_{14}N_2Cl_2$: C, 61.5; H, 4.8; N, 9.6; Cl, 24.2%. Found C, 61.2; H, 5.1; N, 9.7; Cl, 24.1%.

EXAMPLE 13
1-Amino-8-chloro-3-phenyl-3,4-dihydroisoquinoline hydrochloride, prepared using 2-chloro-6-methylbenzonitrile and benzaldehyde; m.p. 247–249° C.

EXAMPLE 14
1-Amino-3-(4-(fluoro)phenyl)-3,4-dihydroisoquinoline hydrochloride, prepared using 2-methylbenzonitrile and 4-fluorobenzaldehyde; m.p. 246–247° C.

EXAMPLE 15
1-Amino-3-(3-(fluoro)phenyl)-3,4-dihydroisoquinoline hydrochloride, prepared using 2-methylbenzonitrile and 3-fluorobenzaldehyde; colourless foam. $(M+H)^+$ 240. Calc. for $C_{15}H_{14}N_2ClF+0.30$ mol $H_2O$: C, 63.9; H, 5.0; N, 9.9%. Found C, 63.9; H, 5.2; N, 9.9%.

EXAMPLE 16
1-Amino-5-fluoro-3-phenyl-3,4-dihydroisoquinoline hydrochloride, prepared using 3-fluoro-2-methylbenzonitrile and benzaldehyde; m.p. 181–184° C.

EXAMPLE 17
1-Amino-8-fluoro-3-phenyl-3,4-dihydroisoquinoline hydrochloride, prepared using 2-fluoro-6-methylbenzonitrile and benzaldehyde; pale yellow foam. $(M+H)^+$ 241. Calc. for $C_{15}H_{14}N_2Cl$: C, 65.1; H, 5.1; N, 10.1%. Found C, 64.9; H, 5.4; N, 9.9%.

EXAMPLE 18
1-Amino-6-bromo-3-phenyl-3,4-dihydroisoquinoline hydrochloride, prepared using 4-bromo-2-methylbenzonitrile and benzaldehyde; m.p. 224–225° C.

EXAMPLE 19
1-Amino-3-(2-(methyl)phenyl)-3,4-dihydroisoquinoline hydrochloride, prepared using 2-methylbenzonitrile and 2-methylbenzaldehyde; colourless foam. $M^+$ 236. Calc. for $C_{16}H_{17}N_2Cl+0.2$ mol $H_2O$: C, 69.5; H, 6.35; N, 10.1; Cl, 12.8%. Found C, 69.4; H, 6.5; N, 10.3; Cl, 12.3%.

EXAMPLE 20
1-Amino-7-methyl-3-phenyl-3,4-dihydroisoquinoline hydrochloride, prepared using 2,5-dimethylbenzonitrile and benzaldehyde; colourless foam. $M^+$ 236. Calc. for $C_{16}H1_{17}N_2Cl$: C, 70.45; H, 6.3; N, 10.3%. Found C, 70.6; H, 6.3; N, 10.4%.

EXAMPLE 21
1-Amino-5-methyl-3-phenyl-3,4-dihydroisoquinoline hydrochloride, prepared using 2,3-dimethylbenzonitrile and benzaldehyde; m.p. 211–212° C.

EXAMPLE 22
1-Amino-3-(2-furyl)-3,4-dihydroisoquinoline hydrochloride, prepared using 2-methylbenzonitrile and 2-furaldehyde; m.p. 208–211° C.

EXAMPLE 23
1-Amino-3-(3-furyl)-3,4-dihydroisoquinoline hydrochloride, prepared using 2-methylbenzonitrile and 3-furaldehyde; m.p. 188–190° C.

EXAMPLE 24
1-Amino-3-(2-thienyl)-3,4-dihydroisoquinoline hydrochloride, prepared using 2-methylbenzonitrile and 2-thiophene carboxaldehyde; m.p. 200–202° C.

EXAMPLE 25
1-Amino-3-(3-thienyl)-3,4-dihydroisoquinoline, prepared using 2-methylbenzonitrile and 3-thiophene carboxaldehyde; m.p. 101–103° C.

EXAMPLE 26
1-Amino-8-chloro-3-(2-furyl)-3,4-dihydroisoquinoline hydrochloride, prepared using 2-chloro-6-methylbenzonitrile and 3-thiophene carboxaldehyde; m.p. 229–231° C.

EXAMPLE 27
1-Amino-3-(3-pyridyl)-3,4-dihydroisoquinoline hydrochloride, prepared using 2-methylbenzonitrile and 3-pyridine carboxaldehyde; pale yellow foam. $M^+$ 223. Calc. for $C_{14}H_{14}N_3Cl$: C, 64.7; H, 5.4; N, 16.2%. Found C, 64.9; H, 5.8; N, 15.9%.

EXAMPLE 28
1-Amino-3-(4-pyridyl)-3,4-dihydroisoquinoline hydrochloride, prepared using 2-methylbenzonitrile and 4-pyridine carboxaldehyde; m.p. 238–241° C.

EXAMPLE 29
1-Amino-3-cyclopropyl-3,4-dihydroisoquinoline hydrochloride, prepared using 2-methylbenzonitrile and cyclopropyl carboxaldehyde; m.p. 200–202° C.

EXAMPLE 30
1-Amino-3-(2-(dimethylamino)methyl)phenyl-3,4-dihydroisoquinoline hydrochloride, prepared using 2-methylbenzonitrile and the intermediate of Example K(b); m.p. 117–119 ° C.

EXAMPLE 31
1-Amino-3-(3-(dimethylamino)methyl)phenyl-3,4-dihydroisoquinoline hydrochloride, prepared using 2-methylbenzonitrile and the intermediate of Example L(b); oxalate m.p. 170–171° C.

EXAMPLE 32
1-Amino-3-(2-benzothiazolyl)-3,4-dihydroisoquinoline hydrochloride, prepared using 2-methylbenzonitrile and 2-benzothiazole carboxaldehyde; m.p. 258–260° C.

EXAMPLE 33
1-Amino-8-chloro-3-(4-fluorophenyl)-3,4-dihydroisoquinoline hydrochloride, prepared using 2-chloro-6-methylbenzonitrile and 4-fluorobenzaldehyde; m.p. 176–178° C.

EXAMPLE 34
1-Amino-3-(phenylethynyl)-3,4-dihydroisoquinoline hydrochloride, prepared using 2-methylbenzonitrile and phenyl propynal; m.p. 235–236° C.

EXAMPLE 35
1-Amino-8-methyl-3-phenyl-3,4-dihydroisoquinoline hydrochloride, prepared using 2,6-dimethylbenzonitrile and benzaldehyde; m.p. 145–147° C.

EXAMPLE 36
1-Amino-5-fluoro-3-(4-fluorophenyl)-3,4-dihydroisoquinoline hydrochloride, prepared using the intermediate of Example B(a) and 4-fluorobenzaldehyde; m.p. 235–237° C.

EXAMPLE 37
1-Amino-8-fluoro-3-(4-fluorophenyl)-3,4-dihydroisoquinoline hydrochloride, prepared using the intermediate of Example C and 4-fluorobenzaldehyde; $M^+$ 258; 360 MHz $^1$H n.m.r ($d_6$-DMSO) 7.48 (1H, m), 7.39 (2H, m), 7.08 (4H, m), 4.69 (1H, dd, J 11.7, 4.7 Hz), 3.04 (2H, ddd, 15.8, 11.7, 4.7 Hz).

EXAMPLE 38
1-Amino-5,8-difluoro-3-(4-fluorophenyl)-3,4-dihydroisoquinoline hydrochloride, prepared using the intermediate of Example D and 4-fluorobenzaldehyde; m.p. 221–223° C.

EXAMPLE 39
1-Amino-6-fluoro-3-(4-fluorophenyl)-3,4-dihydroisoquinoline hydrochloride, prepared using 4-fluoro-2-methylbenzonitrile and 4-fluorobenzaldehyde; m.p. 227–228° C.

EXAMPLE 40
1-Amino-7-fluoro-3-(4-fluorophenyl)-3,4-dihydroisoquinoline hydrochloride This was prepared by the method of Example 1 using 3-fluoro-6-methyl-2-trimethylsilylbenzonitrile (Example F), to give a 9:1 mixture of title compound and the corresponding 8-trimethylsilyl substituted compound. This was purified by the following procedure: the contaminated product (570 mg) in THF (8 ml) was treated with tetra-n-butylammonium fluoride (1.0M in THF, 2.0 ml) and stirred at room temperature for 16 h. The mixture was evaporated and purified by flash chromatography on untreated neutral alumina, eluting with 2% methanol in dichloromethane, increasing the gradient to 100% methanol to give a pale yellow oil which triturated with dichloromethane to afford a fine white powder (270 mg), $M^+$ 258; 360 MHz $^1$H n.m.r ($d_6$-DMSO) 9.29 (1H, br.s), 8.11 (1H, dd, J 2.3, 9.7 Hz), 7.62–7.43 (4H, m), 7.26–7.21 (2H, m), 5.05 (1H, dd, J 5.6, 8.5 Hz), 3.34–3.22 (2H, m).

EXAMPLE 41
1-Amino-3-ethynyl-3,4-dihydroisoquinoline hydrochloride a) 1-Amino-3-(trimethylsilylethynyl)-3,4-dihydroisoquinoline hydrochloride, prepared by the method of Example 1 using 2-methylbenzonitrile and trimethylsilylacetylene carboxaldehyde; m.p. 230–232° C.

b) 1-Amino-3-ethynyl-3,4-dihydroisoquinoline hydrochloride

A mixture of 1-amino-3-(trimethylsilylethynyl)-3,4-dihydroisoquinoline hydrochloride, the intermediate of Example 41(a), and potassium carbonate (100 mg) in methanol (60 ml) was stirred at room temperature for 74 h. More potassium carbonate (630 mg) was added, stirring continued for 16 h, the solution concentrated under vacuum and purified by flash chromatography on untreated neutral alumina, eluting with 5% methanol in dichloromethane, increasing the gradient to 10% methanol in dichloromethane to give a yellow/brown solid (0.75 g). This was recrystallised from methanol/dichloromethane to afford 1-amino-3-ethynyl-3,4-dihydroisoquinoline hydrochloride as yellow crystals, m.p. 226–227° C.

EXAMPLE 42

1-Amino-3-(4-(3-aminopropyloxy)phenyl)-3,4-dihydroisoquinoline hydrochloride a) 1-Amino-3-(4-(3-azidopropyloxy)phenyl)-3,4-dihydroisoquinoline hydrochloride, prepared by the method of Example 1 using 2-methylbenzonitrile and the intermediate of Example G(b); pale yellow oil. (M+H)$^+$ 322; 360 MHz 1H n.m.r (d$_6$-DMSO) 10.26 (1H, br.s), 9.57 (1H, br.s), 9.02 (1H, br.s), 8.13 (1H, d, J 7.9 Hz), 7.69 (1H, t, J 7.5 Hz), 7.52 (1H, t, J 7.7 Hz), 7.45 (1H, d, J 7.7 Hz), 7.31 (2H, d, J 8.0 Hz), 6.96 (1H, d, J 6.8 Hz), 4.95 (1H, t, J 6.8 Hz), 4.14–4.01 (2H, m), 3.79–3.76 (1H, m), 3.51–3.48 (1H, m), 3.28 (2H, d, J 7 Hz), 2.16–2.13 (1H, m), 1.98–1.94 (1H, m).

b) 1-Amino-3-(4-(3-aminopropyloxy)phenyl)-3,4-dihydroisoquinoline hydrochloride

A mixture of 1-amino-3-(4-(3-azidopropyloxy)phenyl)-3,4-dihydroisoquinoline hydrochloride (360 mg, 1.01 mmol) [Example 42(a)] and tin (II) chloride (330 mg, 1.51 mmol) was stirred at room temperature for 30 min. The solution was evaporated, taken up in a mixture of water/methanol/trifluoroacetic acid (85:15:0.5), the precipitate filtered through cotton wool, evaporated and purified by RP-HPLC to give 1-amino-3-(4-(3-aminopropyloxy))phenyl-3,4-dihydroisoquinoline dihydrochloride (195 mg) as a white solid, m.p. 180–182° C.

The compounds of Example 43–44 were prepared by the method of Example 42 using the appropriate isoquinoline.

EXAMPLE 43

1-Amino-3-(3-(2-aminoethyl)phenyl)-3,4-dihydroisoquinoline dihydrochloride a) 1-Amino-3-(3-(2-azidoethyl))phenyl-3,4-dihydroisoquinoline hydrochloride, prepared by the method of Example 1 using 2-methylbenzonitrile and the intermediate of Example H(d); colourless foam, (M+H)$^+$ 292.

b) 1-Amino-3-(3-(2-aminoethyl)phenyl)-3,4-dihydroisoquinoline dihydrochloride, m.p. 97–100° C.

EXAMPLE 44

1-Amino-3-(4-(2-aminoethyl)phenyl)-3,4-dihydroisoquinoline hydrochloride a) 1-Amino-3-(4-(2-azidoethyl)phenyl)-3,4-dihydroisoquinoline hydrochloride, prepared by the method of Example 1 using 2-methylbenzonitrile and the intermediate of Example J(c); yellow foam, (M+H)$^+$ 292.

b) 1-Amino-3-(4-(2-aminoethyl)phenyl)-3,4-dihydroisoquinoline hydrochloride, m.p. 206–209° C.

EXAMPLE 45

1-Amino-3-(3-(3-aminopropyl)phenyl)-3,4-dihydroisoquinoline hydrochloride a) 1-Amino-3-(3-(3-azidopropyl)phenyl)-3,4-dihydroisoquinoline hydrochloride, prepared by the method of Example 1 using 2-methylbenzonitrile and the intermediate of Example I(f); colourless viscous oil, (M+H)$^+$ 306.

b) 1-Amino-3-(3-(3-aminopropyl)phenyl)-3,4-dihydroisoquinoline hydrochloride, colourless solid. (M+H)$^+$ 280; 360 MHz $^1$H n.m.r (d$_6$-DMSO) 10.38 (1H, br.s), 9.64 (1H, br.s), 9.08 (1H, br.s), 8.14 (1H, d, J 7.9), 8.02 (2H, br.s), 7.70 (1H, t, J 7.5 Hz), 7.53 (1H, t, J 7.7 Hz), 7.46 (1H, d, J 7.5 Hz), 7.33 (1H, t, J 7.6 Hz), 7.31 (1H, s), 7.21 (1H, t, J 7.8 Hz), 4.99 (1H, t, J 5.7 Hz), 3.35–3.28 (2H, m), 2.75 (2H, br.s), 2.65 (2H, t, J 7.6 Hz), 1.86 (2H, pentet, J 7 Hz).

EXAMPLE 46

1-Amino-3-(2-thiazolyl)-3,4-dihydroisoquinoline hydrochloride a) Amino-3-(2-(5-trimethylsilyl)thiazolyl)-3,4-dihydroisoquinoline hydrochloride, prepared by the method of Example 1 using 2-methylbenzonitrile and the intermediate of Example P; brown foam. M$^+$ 301.

b) 1-Amino-3-(2-thiazolyl)-3,4-dihydroisoquinoline hydrochloride

Tetra-n-butylammonium flouride (1.0M in THF, 1.78 ml) was added dropwise to a solution of 1-amino-3-(2-(5-trimethylsilyl)thiazolyl)-3,4-dihydroisoquinoline hydrochloride [Example 46(a)] (430 mg, 1.27 mmol). The mixture was stirred at room temperature for 30 min., concentrated under vacuum and the resulting crude material purified by flash chromatography on untreated neutral alumina, eluting with 10% ethanol in dichloromethane, increasing the gradient to 100% ethanol, to give a yellow foam (237 mg). Trituration from dichloromethane and THF gave an off-white solid, m.p. 219–221° C. (dec.).

EXAMPLE 47

1-Amino-3-(2-imidazolyl)-3,4-dihydroisoquinoline hydrochloride a) 1-Amino-3-(2-(N-(2-trimethylsilylethoxymethyl))imidazolyl)-3,4-dihydroisoquinoline hydrochloride, prepared using 2-methylbenzonitrile and 2-(N-(2-trimethylsilylethoxymethyl))imidazole carboxaldehyde; m.p. 134–135° C.

b) 1-Amino-3-(2-imidazolyl)-3,4-dihydroisoquinoline hydrochloride 3N aqueous hydrochloric acid (10 ml) was added to a solution of 1-amino-3-(2-(N-(2-trimethylsilylethoxymethyl))imidazolyl)-3,4-dihydroisoquinoline hydrochloride [(Example 47(a)] (650 mg, 1.7 mmol) in ethanol (50 ml) and the mixture heated to reflux for 20 h, allowed to cool and concentrated under vacuum to afford a yellow foam. This was recrystallised from methanol/diethyl ether to yield pale yellow crystals (350 mg), m.p. 181–182° C.

EXAMPLE 48

1-Amino-3-(4-piperidyl)-3,4-dihydroisoquinoline hydrochloride

A slurry of platinum oxide (8 mg, 10 moll) in methanol (1 ml) was added to a solution of 1-amino-3-(4-pyridyl)-3,4-dihydroisoquinoline hydrochloride (Example 28) (150 mg, 0.578 mmol) in methanol and concentrated hydrochloric acid (0.4 ml), and stirred under 3 atmospheres of hydrogen for 16 h. The mixture was filtered through celite and evaporated. The residue was purified by RP-HPLC to yield a white hygroscope solid (126 mg). [M+H]$^+$ 230; 360 MHz $^1$H n.m.r (d$_6$-DMSO) 10.30 (1H, s), 9.43 (1H, s), 9.03 (1H, s), 8.80 (1H, br.s), 8.56 (1H, br.s), 8.05 (1H, d, J 7.8 Hz), 7.71 (1H, t, J 7.5 Hz), 7.54–7.50 (2H, m), 3.72–3.68 (1H, m), 3.27 (2H, d, J 13.2 Hz), 3.15 (1H, dd, J 17, 4 Hz), 2.99 (1H, dd, J 17.2, 6.9 Hz), 2.80–2.74 (2H, m), 1.95–1.63 (3H, m), 1.48–1.38 (2H, m).

EXAMPLE 49

1-Amino-3-methyl-3,4-dihydroisoquinoline hydroiodide

A mixture of 1-ethylthio-3,4-dihydro-3-methylisoquinoline (M. Gittos et al, *J. Chem. Soc., Perkin I*, 1976, 33) (0.68 g, 3.3 mmol), ammonium iodide (0.48 g, 3.3 mmol) and ammonia (2M in methanol, 4 ml) in ethanol (4 ml) was heated at reflux for 4 h. The mixture was allowed to cool and diethyl ether (100 ml) was added. Some dark oil which separated on standing was decanted and the remain-

EXAMPLE 50

1-Amino-3-(4-hydroxyphenyl)-3,4-dihydroisoquinoline hydrochloride a) 1-Amino-3-(4-(tert-butyldimethylsilyloxy)phenyl)-3,4-dihydroisoquinoline hydrochloride This was prepared by the method of Example 1 using the intermediate of Example M to give a colourless foam, M+ 476; 360 MHz 1H n.m.r (d$_6$-DMSO) 8.12 (1H, d, J 7.9 Hz), 7.70–7.65 (5H, m), 7.53–7.34 (8H, m), 7.19 (2H, d, J 8.6 Hz), 6.74 (2H, d, J 8.6 Hz), 4.86 (1H, dd, J 5.9, 8.6 Hz), 3.28–3.16 (2H, m), 1.03 (9H, s).

b) 1-Amino-3-(4-hydroxyphenyl)-3,4-dihydroisoquinoline hydrochloride

Tetra-n-butylammonium fluoride (1.0M in THF, 3.3 ml) was added to a stirred solution of 1-amino-3-(tert-butyldimethylsilyloxyphenyl)-3,4-dihydroisoquinoline hydrochloride (638 mg, 1.11 mmol) in THF (10 ml). After 15 min., the mixture was evaporated and the residue purified by flash chromatography on untreated neutral alumina, eluting with 5% methanol in dichloromethane, increasing the gradient to 40% methanol in dichloromethane to give a colourless solid (172 mg). This was recrystallised from methanol/dichloromethane (1:2) to give the product as a white powder. M+ 239; 360 MHz $^1$H n.m.r (d$_6$-DMSO) 9.65 (1H, br.s), 8.15 (1H, d, J 7.8 Hz), 7.69 (1H, t, J 7.5 Hz), 7.52 (1H, t, J 7.6 Hz), 7.45 (1H, d, J 7.5 Hz), 7.19 (2H, d, J 8.6 Hz), 6.77 (2H, d, J 8.6 Hz), 4.87 (1H, t, J 7.3 Hz), 3.25 (2H, d, J 7.3 Hz).

EXAMPLE 51

7-Amino-5-phenyl-4,5-dihydrothieno[2,3-c]pyridine hydrochloride a) 7-Amino-5-phenyl-2-trimethylsilyl-4,5-dihydrothieno[2,3-c]pyridine hydrochloride Lithium hexamethyldisilylazide (1.0M in THF, 2.56 ml, 2.56 mmol) was added dropwise to a stirred solution of benzaldehyde (0.26 ml, 2.6 mmol) in dry THF (5 ml), at −10° C., and the imine solution allowed to warm to 0° C. over a period of 2 h. Meanwhile, n- butyllithium (1.45 M in hexanes, 2.56 mmol, 1.77 ml) was added dropwise to a stirred solution of diisopropyl amine (0.40 ml, 2.8 mmol) in dry THF (10 ml) at between −5 and 0 C and the solution stirred for 30 min. DMPU (0.55 ml, 4.6 mmol) was added, the mixture was cooled to −78° C. and a solution of 2-cyano-3-methyl-5-trimethylsilylthiophene (2.56 mmol, 0.500 g) in THF (2 ml) was added dropwise. The orange anion was stirred for 30 min., and the freshly prepared imine solution added dropwise. After 30 min., the mixture was warmed to 0° C. over 30 min., quenched with 6N aqueous hydrochloric acid, extracted twice with dichloromethane, the combined extracts dried over sodium sulphate and evaporated to afford a yellow oil. This was purified by flash chromatography on untreated neutral alumina, eluting with 5% methanol in dichloromethane, increasing the gradient to 10% methanol in dichloromethane to give the title compound as an oily white solid (243 mg). M+ 300; 360 MHz $^1$H n.m.r. (CDCl$_3$) 7.40–7.32 (5H, m), 7.11 (1H, s), 4.96 (1H, dd, J 5.7, 10.8 Hz), 3.28 (1H, dd, J 5.8, 16.7 Hz), 3.17–3.1 (1H, m), 0.36 (9H, s).

b) 7-Amino-5-phenyl-4,5-dihydrothieno[2.3-c]pyridine hydrochloride

Tetra-n-butylammonium fluoride (1.0M in THF, 1.12 ml), was added dropwise to a solution of 7-amino-5-phenyl-2-trimethylsilyl-4,5-dihydrothieno[2,3-c]pyridine hydrochloride (0.13 g, 0.37 mmol) in THF (2.5 ml) and the mixture stirred for 30 min., evaporated and the residue purified by flash chromatography on untreated neutral alumina, eluting with 4% methanol in dichloromethane, increasing the gradient by increments to 20% methanol in dichloromethane to afford a colourless glass. Recrystallisation from dichloromethane gave the title compound as white crystals (51 mg), m.p. 234–236° C.

The compounds of Examples 52–64 were prepared from 2-cyano-3-methyl-5-trimethylsilylthiophene and the appropriate aldehyde using the method of Example 51.

EXAMPLE 52

7-Amino-5-(3-pyridyl)-4,5-dihydrothieno[2,3-c]pyridine hydrochloride a) 7-Amino-5-(3-pyridyl)-2-trimethylsilyl-4,5-dihydrothieno[2,3-c]pyridine hydrochloride, prepared using 3-pyridine carboxaldehyde, pale yellow foam. (M+H)+ 302; 360 MHz 1H n.m.r. (CDCl$_3$) 8.43–8.41 (1H, m), 7.72 (1H, d, J 7.9 Hz), 7.20 (1H, dd, J 4.8, 7.9 Hz), 6.96 (1H, s), 4.91 (1H, dd, J 5.8, 10.0 Hz), 3.20 (1H, dd, J 5.8, 16.7 Hz), 3.02 (1H, dd, J 10.1, 16.7 Hz), 0.20 (9H, s).

b) 7-Amino-5-(3-pyridyl)-4,5-dihydrothieno[2,3-c]pyridine hydrochloride. m.p. 201–202 ° C.

EXAMPLE 53

7-Amino-5-cyclopropyl-4,5-dihydrothieno[2,3-c]pyridine hydrochloride a) 7-Amino-5-cyclopropyl-2-trimethylsilyl-4,5-dihydrothieno[2,3-c]pyridine hydrochloride, prepared using cyclopropyl carboxaldehyde, pale yellow foam. (M+H)+ 265; 360 MHz 1H n.m.r. (CDCl$_3$) 7.12 (1H, s), 3.17–3.11 (1H, m), 3.03–2.92 (2H, m), 1.16–1.12 (1H, m), 0.80–0.76 (1H, m), 0.68–0.64 (1H, m), 0.58–0.54 (1H, m), 0.37 (9H, s), 0.36–0.29 (1H, m).

b) 7-Amino-5-cyclopropyl-4,5-dihydrothieno[2,3-c] pyridine hydrochloride, m.p. 268–270

EXAMPLE 54

7-Amino-5-(3-furyl)-4,5-dihydrothieno[2,3-c]pyridine hydrochloride a) 7-Amino-5-(3-furyl)-2-trimethylsilyl-4,5-dihydrothieno[2,3-c]pyridine hydrochloride, prepared using 3-furaldehyde, pale yellow foam. (M+H)+ 291; 360 MHz $^1$H n.m.r. (CDCl$_3$) 7.54 (1H, s), 7.40 (1H, s), 7.14 (1H, s), 6.46 (1H, s), 4.93 (1H, dd, J 5.7, 10.0 Hz), 3.28 (1H, dd, J 5.7, 16.6 Hz), 3.10 (1H, dd, J 10.0, 16.6 Hz), 0.36 (9H, s).

b) 7-Amino-5-(3-furyl)-4,5-dihydrothieno[2,3-c]pyridine hydrochloride, m.p. 225° C. (dec.).

EXAMPLE 55

7-Amino-5-(2-furyl)-4,5-dihydrothieno[2,3-c]pyridine hydrochloride a) 7-Amino-5-(2-furyl)-2-trimethylsilyl-4,5-dihydrothieno[2,3-c]pyridine hydrochloride, using 2-furaldehyde, pale yellow foam, M+ 290; 360 MHz $^1$H n.m.r. (d$_6$-DMSO) 7.69 (1H, s), 7.45 (1H, s), 6.45 (1H, dd, J 1.8, 3.2 Hz), 6.36 (1H, d, J 3.3 Hz), 5.18 (1H, t, J 6.7 Hz), 3.43–3.29 (2H, m), 0.35 (9H, s).

b) 7-Amino-5-(2-furyl)-4,5-dihydrothieno[2,3-c]pyridine hydrochloride, m.p. 252–254° C.

EXAMPLE 56

7-Amino-5-(2-thienyl)-4,5-dihydrothieno[2,3-c]pyridine hydrochloride a) 7-Amino-5-(2-thienyl)-2-trimethylsilyl-4,5-dihydrothieno[2.3-c]pyridine hydrochloride, using 2-thiophene carboxaldehyde.

b) 7-Amino-5-(2-thienyl)-4,5-dihydrothieno[2,3-c]pyridine hydrochloride. m.p. 243–245° C.

EXAMPLE 57
7-Amino-5-(1-benzyl-2-pyrrolyl)-4,5-dihydrothieno[2,3-c]pyridine hydrochloride
a) 7-Amino-5-(1-benzyl-2-pyrrolyl)-2-trimethylsilyl-4,5-dihydrothieno[2,3-c]pyridine hydrochloride, using 1-benzyl-2-pyrrolyl carboxaldehyde.
b) 7-Amino-5-(1-benzyl-2-pyrrolyl)-4,5-dihydrothieno[2,3-c]pyridine hydrochloride, m.p. 250–252° C.

EXAMPLE 58
7-Amino-5-(1-methyl-2-pyrrolyl)-4,5-dihydrothieno[2,3-c]pyridine hydrochloride
a) 7-Amino-5-(1-methyl-2-pyrrolyl)-2-trimethylsilyl-4,5-dihydrothieno[2,3-c]pyridine hydrochloride, using 1-methyl-2-pyrrolyl carboxaldehyde.
b) 7-Amino-5-(1-methyl-2-pyrrolyl)-4,5-dihydrothieno[2,3-c]pyridine hydrochloride, m.p. 224–225° C.

EXAMPLE 59
7-Amino-5-ethynyl-4,5-dihydrothieno[2,3-c]pyridine hydrochloride
a) 7-Amino-5-ethynyl-2-trimethylsilyl-4,5-dihydrothieno[2,3-c]pyridine hydrochloride, prepared using trimethylsilylacetylene carboxaldehyde, white solid, $M^+$ 320.
b) 7-Amino-5-ethynyl-4,5-dihydrothieno[2,3-c]pyridine hydrochloride, m.p. 268–270° C.

EXAMPLE 60
7-Amino-5-propynl-4,5-dihydrothieno[2,3-c]pyridine hydrochloride
a) 7-Amino-5-propynyl-2-trimethylsilyl-4,5-dihydrothieno[2,3-c]pyridine hydrochloride, prepared using 2-butynal, brown gum, $M^+$ 262; 360 MHz $^1$H n.m.r. (CDCl$_3$) 7.13 (1H, s), 4.64 (1H, m), 3.14 (2H, ddd, J 16.5, 7.9, 5.9 Hz), 1.78 (3H, d, J 2.2 Hz), 0.37 (9H, s).
b) 7-Amino-5-propynyl-4,5-dihydrothieno[2,3-c]pyridine hydrochloride, m.p. 226–227° C.

EXAMPLE 61
7-Amino-5-(2-thiazolyl)-4,5-dihydrothieno[2,3-c]pyridine hydrochloride
a) 7-Amino-5-(2-(5-trimethylsilyl)thiazolyl)-2-trimethylsilyl-4,5-dihydrothieno[2,3-c]pyridine hydrochloride, prepared from the intermediate of Example P, brown glass, $[M+H]^+$ 380; 360 MHz 1H n.m.r. (CDCl$_3$) 7.50 (1H, s), 6.92 (1H, s), 5.17 (1H, dd, J 6.5, 5.1 Hz), 3.37 (2H, ddd, J 16.9, 6.7, 4.9 Hz), 0.14 (9H, s), 0.09 (9H, s).
b) 7-Amino-5-(2-thiazolyl)-4,5-dihydrothieno[2,3-c]pyridine hydrochloride, pale yellow foam. $[M+H]^+$ 336. Calc. for $C_{10}H_{10}N_3S_2Cl$+0.5 mol hydrochloric acid+2 mol $H_2O$: C, 33.1; H, 4.3; N, 11.6%. Found C, 33.0; H, 4.55; N, 11.5%.

EXAMPLE 62
7-Amino-5-(3,3-dimethylbutynl)-4,5-dihydrothieno[2,3-c]pyridine hydrochloride
a) 7-Amino-5-(tert-butylethynyl)-2-trimethylsilyl-4,5-dihydrothieno[2,3-c]pyridine hydrochloride, prepared using 4,4-dimethylpent-2-ynal, yellow glass, $[M+H]^+$ 305; 360 MHz $^1$H n.m.r. (CDCl$_3$) 7.12 (1H, s), 4.61 (1H, dd, J 9.1, 5.7 Hz), 3.12 (2H, ddd, J 16.4, 9.1, 5.6 Hz), 1.16 (9H, s), 0.37 (9H, s).
b) 7-Amino-5-(tert-butylethynyl)-4,5-dihydrothieno[2,3-c]pyridine hydrochloride, yellow foam. $[M+H]^+$ 223. Calc. for $C_{13}H_{17}N_2SCl$: C, 58.1; H, 6.4; N, 10.4; S, 11.9; Cl, 13.2%. Found C, 58.15; H, 6.6; N, 10.1; S, 11.6; Cl, 13.2%.

EXAMPLE 63
7-Amino-5-(phenylethynyl)-4,5-dihydrothieno[2,3-c]pyridine hydrochloride
a) 7-Amino-5-(phenylethynyl)-2-trimethylsilyl-4,5-dihydrothieno[2,3-c]pyridine hydrochloride, prepared using phenyl propynal, brown foam, $M^+$ 324.
b) -Amino-5-(phenylethynyl)-4,5-dihydrothieno[2,3-c]pyridine hydrochloride, brown waxy solid. $[M+H]^+$ 253. Calc. for $C_{15}H_{13}N_2SCl$+0.5 mol HCl+0.5 mol $H_2O$: C, 57.0; H, 4.6; N, 8.9; S, 10.1%. Found C, 56.8; H, 4.5; N, 8.5; S, 9.9%.

EXAMPLE 64
7-Amino-5-(cyclobutyl)-4,5-dihydrothieno[2,3-c]pyridine hydrochloride
a) 7-Amino-5-(cyclobutyl)-2-trimethylsilyl-4,5-dihydrothieno[2,3-c]pyridine hydrochloride, prepared using cyclobutyl carboxaldehyde, orange gum, $M^+$ 278.
b) 7-Amino-5-(cyclobutyl)-4,5-dihydrothieno[2,3-c]pyridine hydrochloride, yellow crystals, m.p.>260° C. $[M+H]^+$ 207; 360 MHz $^1$H n.m.r. (d$_6$-DMSO) 8.89 (1H, br.s), 8.14 (1H, d, J 4.9 Hz), 7.22 (1H, d, J 4.9 Hz), 3.76 (1H, q, J 8.0 Hz), 3.07 (2H, dd, J 17, 5.8 Hz), 2.66 (2H, dd, J 17, 9.5 Hz), 2.45 (1H, q, J 8.2 Hz), 1.99 (2H, m), 1.84 (4H, m).

EXAMPLE 65
7-Amino-5-ethynyl-2-methyl-4,5-dihydrothieno[2,3-c]pyridine hydrochloride.
a) 7-Amino-5-trimethylsilylethynyl-2-methyl-4,5-dihydrothieno[2,3-c]pyridine hydrochloride This was prepared from 2,5-dimethyl-3-cyanothiophene and trimethylsilylacetylene carboxaldehyde, according to the procedure of Example 51(a) to afford a yellow/brown solid, $M^+$ 299.

b) 7-Amino-5-ethynyl-2-methyl-4,5-dihydrothieno[2,3-c]pyridine hydrochloride.

This was prepared from 7-amino-5-trimethylsilylethynyl-2-methyl-4,5-dihydrothieno[2,3-c]pyridine hydrochloride [Example 62(a)] according to the procedure of Example 51(b) to afford off-white crystals, m.p. 227–230° C. (dec.).

EXAMPLE 66
7-Amino-5-ethyl-4,5-dihydrothieno[2,3-c]pyridine hydrochloride

Palladium on charcoal (57 mg) was added as a slurry in ethanol to 7-amino-5-ethynyl-4,5-dihydrothieno[2,3-c]pyridine hydrochloride (Example 56) (113 mg, 0.531 mmol) in ethanol (6 ml) and the mixture stirred for 16 h under 3 atm. of hydrogen. The mixture was then filtered through celite, evaporated and triturated with dichloromethane to afford a white powder (75 mg), m.p. 221–223° C.

EXAMPLE 67

Following the method of Example 66, the following compound was prepared from 7-amino-5-propynyl-4,5-dihydrothieno[2,3-c]pyridine hydrochloride (Example 60): 7-Amino-5-propyl-4,5-dihydrothieno[2,3-c]pyridine hydrochloride, off-white solid, $M^+$ ($^+$EI) 194; 360 MHz $^1$H n.m.r. (d$_6$-DMSO) 9.30 (1H, br.s), 8.61 (1H, br.s), 8.14 (1H, d, J 4.9 Hz), 7.23 (1H, d, J 4.9 Hz), 3.82 (1H, m), 2.96 (2H, ddd, J 17, 10, 6 Hz), 1.55 (2H, m), 1.40 (2H, m), 0.90 (3H, t, J 7.2 Hz).

EXAMPLE 68
4-Amino-6-phenyl-6,7-dihydrothieno[3,2-c]pyridine hydrochloride

This was prepared by the method of Example 51, substituting 3-cyano-2-methyl-5-trimethylsilylthiophene for 2-cyano-3-methyl-5-trimethylsilylthiophene and using the appropriate aldehyde:

a) 4-Amino-6-phenyl-2-trimethylsilyl-6,7-dihvdrothieno[3,2-c]pyridine hydrochloride, prepared using benzaldehyde, pale yellow foam (0.44 g). [M+H]$^+$ 301; 360 MHz $^1$H n.m.r (d$_6$-DMSO) 7.98 (1H, s), 7.44–7.22 (5H, m), 5.10 (1H, dd, J 6.0, 9.2 Hz), 3.55 (1H, dd, J 6.0, 17.1 Hz), 3.43–3.34 (1H, m), 0.32 (9H, s).

b) 4-Amino-6-phenyl-6,7-dihydrothieno[3,2-c]pyridine hydrochloride, m.p. 213–215° C.

The compounds of Examples 69–70 were prepared from 3-cyano-2-methyl-5-trimethylsilylthiophene and the appropriate aldehyde using the method of Example 68.

EXAMPLE 69

4-Amino-6-ethynyl-6,7-dihydrothieno[3,2-c]pyridine hydrochloride a) 4-Amino-6-trimethylsilylethynyl-2-trimethylsilyl-6,7-dihydrothieno[3,2-c]pyridine hydrochloride, prepared using trimethylsilylacetylene carboxaldehyde, yellow solid. (M+H$^+$) 321; 360 MHz $^1$H n.m.r (d$_6$-DMSO) 7.87 (1H, s), 4.83 (1H, t, J 6.6 Hz), 3.37 (1H, dd, J 5.9, 17.0 Hz), 3.24–3.18 (1H, m), 0.22 (9H, s), 0.00 (9H, s).

b) 4-Amino-6-ethynyl-6,7-dihydrothieno[3,2-c]pyridine hydrochloride, m.p. 196–197° C.

EXAMPLE 70

4-Amino-6-cyclopropyl-6,7-dihvdrothieno[3,2-c]pyridine hydrochloride a) 4-Amino-6-cyclopropyl-2-trimethylsilyl-6,7-dihydrothieno[3,2-c]pyridine hydrochloride, prepared using cyclopropylcarboxaldehyde, off-white solid. (M+H$^+$) 265; 360 MHz $^1$H n.m.r (d$_6$-DMSO) 9.76 (1H, br s), 9.40 (1H, br s), 8.83 (1H, br s), 7.97 (1H, s), 3.39–3.35 (1H, m), 3.18–3.12 (2H, m), 1.12–1.02 (1H, m), 0.55–0.53 (2H, m), 0.39–0.33 (2H, m), 0.32 (9H, s).

a) 4-Amino-6-cyclopropyl-6,7-dihydrothieno[3,2-c]pyridine hydrochloride, m.p. 236–238° C.

EXAMPLE 71

7-Amino-4,5-dihydrothieno[2,3-c]pyridine a) 7-Methylthio-4,5-dihydro[2,3-c]pyridine hydroiodide To a solution of 4,5-dihydro[2,3-c]pyridin-7(6H)-thione (R. V. Davies et al., *J. Chem. Soc., Perkin 1*, 1976, 138) (11.3 g, 66.8 mmol) in acetone (80 ml) was added iodomethane (7.6 ml, 120 mmol). The solution was stirred for 6 h and the resulting solid was collected to give the title compound as a yellow solid (20.3 g), m.p. 212–5° C. (dec.).

b) 7-Amino-4,5-dihydrothieno[2,3-c]pyridine

A solution of 7-methylthio-4,5-dihydro[2,3-c]pyridine hydroiodide in 150 ml of isopropanol containing conc. aqueous ammonia (15 ml) was heated at reflux for 4 h. After cooling, the solvent was evaporated and the residue was partitioned between diethyl ether (100 ml) and dilute hydrochloric acid. The aqueous phase was basified with aqueous sodium hydroxide and extracted four times with dichloromethane. The combined organic phases were dried over magnesium sulphate and concentrated to give 7.6 g of crude product which partially solidified on standing. This residue was taken up in isopropanol (150 ml) and 6.55 g of oxalic acid dihydrate dissolved in 50 ml of isopropanol was added. After stirring for several hours the solid was collected to give 9.71 g of the title compound as an off-white solid, m.p. 158–160° C. (dec.).

EXAMPLE 72

4-Amino-6,7-dihydrothieno[3,2-c]pyridine hydroiodide a) 4-Methylthio-6,7-dihvdrothieno[3,2-c]pyridine hydroiodide To a stirred solution of phosphoric acid (205 g) at 175° C. was added dropwise 2-(2-thienyl)ethylisothiocyanate (R. V. Davies et al., *J. Chem. Soc., Perkin 1*, 1976, 138). The solution was stirred for 1 h, poured onto ice/water (3 L), the mixture stirred for 3 h to decompose the phosphoric acid, extracted with chloroform, dried over magnesium sulphate and evaporated to give a dark oil which solidified on standing. This solid was taken up in acetone (250 ml) and iodomethane (12 ml) was added. The reaction mixture was stirred for 4 h and the solid was collected to give the title compound as a yellow solid (26 g), m.p. 184–187° C.

b) 4-Amino-6,7-dihydrothieno[3,2-c]pyridine hydroiodide

Ammonia gas was bubbled through a solution of 4-methylthio-6,7-dihydrothieno[3,2-c]pyridine (6.00 g, 19.3 mmol) in isopropanol (40 ml) for 4 h and the resulting solution was allowed to stand for 24 h. The precipitate was filtered off and dissolved in methanol (25 ml), treated with charcoal (1.5 g), filtered and the filtrate diluted with diethyl ether (75 ml). The resulting solid was collected and dried to afford the title compound (1.8 g) as a white solid, m.p. 160–163° C.

According to the invention, these examples and their pharmaceutically acceptable salts, enantiomers and tautomers are useful as pharmaceuticals, and are useful in the manufacture of a medicament for the treatment or prophylaxis of the abovementioned diseases and conditions, eg inflammatory disease. Hence, the invention provides a method of treating, or reducing the risk of, inflammatory disease in a patient suffering from, or at risk of, the disease, wherein the method comprises administering to the patient a compound exemplified above, or a pharmaceutically acceptable salt, enantiomer and tautomer thereof.

Screen

The activity of compounds according to the invention was tested in the following screen.

The activity of compounds of formula I, or a pharmaceutically acceptable salt, enantiomer or tautomer thereof, may be screened for nitric oxide synthetase activity by a procedure based on that of Förstennann et al. (1992) Eur. J. Pharm. 225, 161–165. Nitric oxide synthetase converts $^3$H-L-arginine to $^3$H-L-citrulline which can be separated by cation exchange chromatography and quantified by liquid scintillation counting.

Enzyme is prepared, after induction, from the cultured murine macrophage cell line J774A-1 (obtained from the laboratories of the Imperial Cancer Research Fund). J774A-1 cells are cultured in Dulbeccos Modified Eagles Medium (DMEM) supplemented with 10% foetal bovine serum, 4 mM L-glutamine and antibiotics (100 units/ml penicillin G, 100 mg/ml streptomycin & 0.25 mg/ml amphotericin B). Cells are routinely grown in 225 cm$^2$ flasks containing 35 ml medium kept at 37° C. and in a humidified atmosphere containing 5% $CO_2$. Nitric oxide synthase is produced by cells in response to interferon-g (IFNg) and lipopolysaccharide (LPS). The medium from confluent culture flasks is removed and replaced with 25 ml (per flask) of fresh medium containing 1 mg/ml LPS and 10 units/ml IFNg. After a period of 17–20 hours in culture, harvesting of cells is accomplished by scraping the cell sheet from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v)

Triton-X-100, 0.1 mM dithiothreitol and a cocktail of protease inhibitors comprising leupeptin (2 mg/ml), soya bean trypsin inhibitor (10 mg/ml), aprotinin (5 mg/ml) & phenylmethylsulphonyl fluoride (50 mg/ml).

For the assay, 25 $\mu$l substrate cocktail (50 mM Tris-HCl (pH 7.5 at 20° C.), 400 $\mu$M NADPH, 20 $\mu$M flavin adenine dinucleotide, 20 $\mu$M flavin mononucleotide, 4 $\mu$M tetrahydrobiopterin, 12 $\mu$M L-arginine and 0.025 mCi L-[$^3$H] arginine) is added to wells of a 96 well filter plate (0.45 $\mu$M pore size) containing 25 $\mu$l of a solution of test compound in 50 mM Tris-HCl. The reaction is started by adding 50 $\mu$l of cell lysate (prepared as above) and after incubation for 1 hour at room temperature is terminated by addition of 50 $\mu$l of an aqueous solution of 3 mM nitroarginine and 21 mM EDTA.

Labelled L-citrulline is separated from labelled L-arginine using Dowex AG-SOW. 150 $\mu$l of a 25% aqueous slurry of Dowex 50W (Na$^+$ form) is added to the assay after which the whole is filtered into 96 well plates. 75 $\mu$l of filtrate is sampled and added to wells of 96 well plates containing solid scintillant. After allowing the samples to dry the L-citrulline is quantified by scintillation counting.

In a typical experiment basal activity is 300 dpm per 75 $\mu$l sample which is increased to 1900 dpm in the reagent controls. Compound activity is expressed as IC$_{50}$ (the concentration of drug substance which gives 50% enzyme inhibition in the assay) and aminoguanidine, which gives an IC$_{50}$ (50% inhibitory concentration) of 10 $\mu$M, is tested as a standard to verify the procedure. Compounds are tested at a range of concentrations and from the inhibitions obtained IC$_{50}$ values are calculated. Compounds that inhibit the enzyme by at least 25% at 100 $\mu$M are classed as being active and are subjected to at least one retest.

In the above mentioned screen, the compounds of Examples 2, 14–17, 22–29, 36–38, 41, 46, 49, 51–56, 58–61 and 64–72 were tested and gave IC$_{50}$ values of less than 25 $\mu$M indicating that they are expected to show useful pharmacological activity.

We claim:

1. A compound of formula I

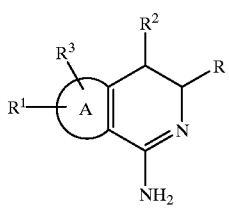

wherein:
R represents
(i) phenyl, benzothiazolyl or a six membered heterocyclic aromatic ring containing 1 to 3 nitrogen atoms, which phenyl, benzo ring of the benzothiazolyl or heterocyclic aromatic ring is optionally substituted by alkyl C1 to 6, alkoxy C1 to 6, halogen, hydroxy, thioalkyl C1 to 6, benzyloxy, or a group —Q(CH$_2$)$_p$NR$^4$R$^5$; or
(ii) alkyl C1 to 8, cycloalkyl C3 to 8, alkynyl C2 to 8, piperidyl, phenylalkyl C7 to 14, which alkyl, cycloalkyl, alkynyl, or piperidyl is optionally substituted by a group —(CH$_2$)$_p$NR$^4$R$^5$, the phenylalkyl being optionally substituted by a group —(CH$_2$)$_p$NR$^5$R$^5$, alkyl C1 to 6, alkoxy C1 to 6, halogen or nitro; or (iii) a 5 membered heterocyclic aromatic ring containing 1 to 3 heteroatoms selected from O, N or S, optionally substituted by alkyl C1 to 6, phenylalkyl C7 to 14 or halogen; or
(iv) hydrogen or phenylalkynyl C7 to 14;
Q represents O, NR$^6$ or a bond;
R$^1$ represents hydrogen, alkyl C1 to 6, alkoxy C1 to 6, trimethylsilyl or halogen;
R$^2$ represents hydrogen, alkyl C1 to 6 or phenyl optionally substituted by alkyl C1 to 6, alkoxy C1 to 6, halogen or hydroxy;
R represents hydrogen or halogen;
R$^4$, R$^5$ and R$^6$ independently represent hydrogen or alkyl C1 to 6,
or —NR$^4$R$^5$ together represents piperidyl, pyrrolidinyl or morpholinyl;
p represents an integer 1 to 5; and
A represents a thieno or benzo ring;
provided that when A represents a benzo ring and Q represents O, p does not represent 1; or a pharmaceutically acceptable salt, enantiomer or tautomer thereof;
provided that when A represents a benzo ring, compounds of formula I in which R represents hydrogen, alkyl C1 to 6 or phenyl, R$^1$ represents hydrogen, alkyl C1 to 6, alkoxy C1 to 6 or halogen, R$^2$ represents hydrogen, alkyl C1 to 6 or unsubstituted phenyl and R$^3$ represents hydrogen are disclaimed.

2. A compound according to claim 1, or a pharmaceutically acceptable salt, enantiomer or tautomer thereof, wherein the compound is a thieno[2,3-c]pyridine or a thieno [3,2-c]pyridine compound of formula I.

3. The compound of claim 1, or a pharmaceutically acceptable salt, enantiomer or tautomer thereof, wherein R represents ethynyl, cyclopropyl, fluorophenyl, benzyloxyphenyl, thiomethylphenyl, methylphenyl, methoxyphenyl, chlorophenyl, furyl, thienyl, pyridyl, phenylethynyl, amionopropyloxyphenyl, aminoethylphenyl, aminopropylphenyl, thiazolyl, imidazolyl, methyl, ((dimethylamino)methyl)phenyl, propynyl, butylethynyl, phenylethynyl, benzylpyrrolyl, methylpyrrolyl, ethyl, cyclobutyl, hydroxyphenyl or propyl.

4. A compound, being:
1-amino-3-(2-fluorophenyl)-3,4-dihydroisoquinoline; or
1-amino-3-phenyl-3,4-dihydroisoquinoline; or
1-amino-3-(4-(benzyloxy)phenyl)-3,4-dihydroisoquinoline; or
1-amino-3-(4-(methylthio)phenyl)-3,4-dihydroisoquinoline; or
1-amino-3-(4-(methyl)phenyl)-3,4-dihydroisoquinoline; or
1-amino-3-(3-(methyl)phenyl)-3,4-dihydroisoquinoline; or
1-amino-3-(4-(methoxy)phenyl)-3,4-dihydroisoquinoline; or
1-amino-5-methoxy-3-phenyl-3,4-dihydroisoquinoline; or
1-amino-3-(2-(chloro)phenyl)-3,4-dihydroisoquinoline; or
1-amino-3-(3-(chloro)phenyl)-3,4-dihydroisoquinoline; or
1-amino-3-(4-(chloro)phenyl)-3,4-dihydroisoquinoline; or
1-amino-5-chloro-3-phenyl-3,4-dihydroisoquinoline; or
1-amino-8-chloro-3-phenyl-3,4-dihydroisoquinoline; or
1-amino-3-(4-(fluoro)phenyl)-3,4-dihydroisoquinoline; or
1-amino-3-(3-(fluoro)phenyl)-3,4-dihydroisoquinoline; or
1-amino-5-fluoro-3-phenyl-3,4-dihydroisoquinoline; or
1-amino-8-fluoro-3-phenyl-3,4-dihydroisoquinoline; or
1-amino-6-bromo-3-phenyl-3,4-dihydroisoquinoline; or
1-amino-3-(2-(methyl)phenyl)-3,4-dihydroisoquinoline; or
1-amino-7-methyl-3-phenyl-3,4-dihydroisoquinoline; or
1-amino-5-methyl-3-phenyl-3,4-dihydroisoquinoline; or 1-amino-3-(2-furyl)-3,4-dihydroisoquinoline; or
1-amino-3-(3-furyl)-3,4-dihydroisoquinoline; or
1-amino-3-(2-thienyl)-3,4-dihydroisoquinoline; or
1-amino-3-(3-thienyl)-3,4-dihydroisoquinoline; or
1-amino-8-chloro-3-(2-furyl)-3,4-dihydroisoquinoline; or
1-amino-3-(3-pyridyl)-3,4-dihydroisoquinoline; or
1-amino-3-(4-pyridyl)-3,4-dihydroisoquinoline; or
1-amino-3-cyclopropyl-3,4-dihydroisoquinoline; or
1-amino-3-(2-(dimethylamino)methyl)phenyl-3,4-dihydroisoquinoline; or
1-amino-3-(3-(dimethylamino)methyl)phenyl-3,4-dihydroisoquinoline; or
1-amino-3-(2-benzothiazolyl)-3,4-dihydroisoquinoline; or
1-amino-8-chloro-3-(4-fluorophenyl)-3,4-dihydroisoquinoline; or
1-amino-3-(phenylethynyl)-3,4-dihydroisoquinoline; or
1-amino-8-methyl-3-phenyl-3,4-dihydroisoquinoline; or
amino-5-fluoro-3-(4-fluorophenyl)-3,4-dihydroisoquinoline; or
amino-8-fluoro-3-(4-fluorophenyl)-3,4-dihydroisoquinoline; or
1-amino-5,8-difluoro-3-(4-fluorophenyl)-3,4-dihydroisoquinoline; or
1-amino-6-fluoro-3-(4-fluorophenyl)-3,4-dihydroisoquinoline; or
1-amino-7-fluoro-3-(4-fluorophenyl)-3,4-dihydroisoquinoline; or
1-amino-3-ethynyl-3,4-dihydroisoquinoline; or
1-amino-3-(4-(3-aminopropyloxy)phenyl)-3,4-dihydroisoquinoline; or
1-amino-3-(3-(2-aminoethyl)phenyl)-3,4-dihydroisoquinoline; or
1-amino-3-(4-(2-aminoethyl)phenyl)-3,4-dihydroisoquinoline; or
1-amino-3-(3-(3-aminopropyl)phenyl)-3,4-dihydroisoquinoline; or
1-amino-3-(2-thiazolyl)-3,4-dihydroisoquinoline; or
1-amino-3-(2-imidazolyl)-3,4-dihydroisoquinoline; or
1amino-3-(4-piperidyl)-3,4-dihydroisoquinoline; or
1-amino-3-methyl-3,4-dihydroisoquinoline; or
1-amino-3-(4-hydroxyphenyl)-3,4-dihydroisoquinoline; or
7-amino-5-phenyl-4,5-dihydrothieno[2,3-c]pyridine; or
7-amino-5-(3-pyridyl)-4,5-dihydrothieno[2,3-c]pyridine; or
7-amino-5-cyclopropyl-4,5-dihydrothieno[2,3-c]pyridine; or
7-amino-5-(3-furyl)-4,5-dihydrothieno[2,3-c]pyridine; or
7-amino-5-(2-furyl)-4,5-dihydrothieno[2,3-c]pyridine; or
7-amino-5-(2-thienyl)-4,5-dihydrothieno[2,3-c]pyridine; or
7-amino-5-(-benzyl-2-pyrrolyl)-4,5-dihydrothieno[2,3-c]pyridine; or
7-amino-5-(1-methyl-2-pyrrolyl)-4,5-dihydrothieno[2,3-c]pyridine; or
7-amino-5-ethynyl-4,5-dihydrothieno[2,3-c]pyridine; or
7-amino-5-propynyl-4,5-dihydrothieno[2,3-c]pyridine; or
7-amino-5-(2-thiazolyl)-4,5-dihydrothieno[2,3 -c]pyridine; or
7-amino-5-(3,3-dimethylbutynyl)-4,5-dihydrothieno[2,3-c]pyridine; or
7-amino-5-phenylethynyl)-4,5-dihydrothieno[2,3-c]pyridine; or
7-amino-5-(cyclobutyl)-4,5-dihydrothieno[2,3-c]pyridine; or
7-amino-5-ethynyl-2-methyl-4,5-dihydrothieno[2,3-c]pyridine; or
7-amino-5-ethyl-4,5-dihydrothieno[2,3-c]pyridine; or
7-amino-5-propyl-4,5-dihydrothieno[2,3-c]pyridine; or
4-amino-6-phenyl-6,7-dihydrothieno[3,2-c]pyridine; or
4-amino-6-ethynyl-6,7-dihydrothieno[3,2-c]pyridine; or
4-amino-6-cyclopropyl-6,7-dihydrothieno[3,2-c]pyridine; or
7-amino-4,5-dihydrothieno[2,3-c]pyridine; or
4-amino-6,7-dihydrothieno[3,2-c]pyridine;
or a pharmaceutically acceptable salt, enantiomer or tautomer thereof.

5. A method of treating, or reducing the risk of, inflammatory disease in a patient suffering from, or at risk of, said disease, wherein the method comprises administering to the patient a compound of formula I

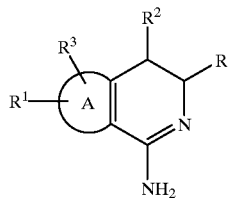

wherein:
R represents
(i) phenyl, benzothiazolyl or a six membered heterocyclic aromatic ring containing 1 to 3 nitrogen atoms, which phenyl, benzo ring of the benzothiazolyl or heterocyclic aromatic ring is optionally substituted by alkyl C1 to 6, alkoxy C1 to 6, halogen, hydroxy, thioalkyl C1 to 6, benzyloxy, or a group —Q(CH$_2$)$_p$NR$^4$R$^5$; or
(ii) alkyl C1 to 8, cycloalkyl C3 to 8, alkynyl C2 to 8, piperidyl, phenylalkyl C7 to 14, which alkyl, cycloalkyl, alkynyl, or piperidyl is optionally substituted by a group —(CH$_2$)$_p$NR$^4$R$^5$, the phenylalkyl being optionally substituted by a group —(CH$_2$)$_p$NR$^4$R$^5$, alkyl C1 to 6, alkoxy C1 to 6, halogen or nitro; or
(iii) a 5 membered heterocyclic aromatic ring containing 1 to 3 heteroatoms selected from O, N or S, optionally substituted by alkyl C1 to 6, phenylalkyl C7 to 12 or halogen; or
(iv) hydrogen or phenylalkynyl C7 to 12;
Q represents O, NR$^6$ or a bond;
R$^1$ represents hydrogen, alkyl C1 to 6, alkoxy C1 to 6, trimethylsilyl or halogen;
R$^2$ represents hydrogen, alkyl C1 to 6 or phenyl optionally substituted by alkyl C1 to 6, alkoxy C1 to 6, halogen or hydroxy;
R$^3$ represents hydrogen or halogen;
R$^4$, R$^5$ and R$^6$ independently represent hydrogen or alkyl C1 to 6,
or —NR$^4$R$^5$ together represents piperidyl, pyrrolidinyl or morpholinyl;
p represents an integer 1 to 5; and
A represents a thieno or benzo ring;
provided that when A represents a benzo ring and Q represents O, p does not represent 1; or a pharmaceutically acceptable salt, enantiomer or tautomer thereof.

6. The method of claim 5, wherein the compound is a thieno[2,3-c]pyridine or a thieno[3,2-c]pyridine compound of formula I.

7. The method of claim 5, wherein R represents ethynyl, cyclopropyl, fluorophenyl, benzyloxyphenyl, thiomethylphenyl, methylphenyl, methoxyphenyl, chlorophenyl, furyl, thienyl, pyridyl, phenylethynyl, amionopropyloxyphenyl, aminoethylphenyl, aminopropylphenyl, thiazolyl, imidazolyl, methyl, ((dimethylamino)methyl)phenyl, propynyl, butylethynyl, phenylethynyl, benzylpyrrolyl, methylpyrrolyl, ethyl, cyclobutyl, hydroxyphenyl or propyl.

8. A method of treating, or reducing the risk of, inflammatory disease in a patient suffering from, or at risk of, said disease, wherein the method comprises administering to the patient a compound, the compound being:
1-amino-3-(2-fluorophenyl)-3,4-dihydroisoquinoline; or
1-amino-3-phenyl-3,4-dihydroisoquinoline; or
1-amino-3-(4-(benzyloxy)phenyl)-3,4-dihydroisoquinoline; or
1-amino-3-(4-(methylthio)phenyl)-3,4-dihydroisoquinoline; or
1-amino-3-(4-(methyl)phenyl)-3,4-dihydroisoquinoline; or
1-amino-3-(3-(methyl)phenyl)-3,4-dihydroisoquinoline; or
1-amino-3-(4-(methoxy)phenyl)-3,4-dihydroisoquinoline; or
1-amino-5-methoxy-3-phenyl-3,4-dihydroisoquinoline; or
1-amino-3-(2-(chloro)phenyl)-3,4-dihydroisoquinoline; or
1-amino-3-(3-(chloro)phenyl)-3,4-dihydroisoquinoline; or
1-amino-3-(4-(chloro)phenyl)-3,4-dihydroisoquinoline; or
1-amino-5-chloro-3-phenyl-3,4-dihydroisoquinoline; or
1-amino-8-chloro-3-phenyl-3,4-dihydroisoquinoline; or
1-amino-3-(4-(fluoro)phenyl)-3,4-dihydroisoquinoline; or
1-amino-3-(3-(fluoro)phenyl)-3,4-dihydroisoquinoline; or
1-amino-5-fluoro-3-phenyl-3,4-dihydroisoquinoline; or
1-amino-8-fluoro-3-phenyl-3,4-dihydroisoquinoline; or
1-amino-6-bromo-3-phenyl-3,4-dihydroisoquinoline; or
1-amino-3-(2-(methyl)phenyl)-3,4-dihydroisoquinoline; or
1-amino-7-methyl-3-phenyl-3;4-dihydroisoquinoline; or
1-amino-5-methyl-3-phenyl-3,4-dihydroisoquinoline; or
1-amino-3-(2-furyl)-3,4-dihydroisoquinoline; or
1-amino-3-(3-furyl)-3,4-dihydroisoquinoline; or
1-amino-3-(2-thienyl)-3,4-dihydroisoquinoline; or
1-amino-3-(3-thienyl)-3,4-dihydroisoquinoline; or
1-amino-8-chloro-3-(2-furyl)-3,4-dihydroisoquinoline; or
1-amino-3-(3-pyridyl)-3,4-dihydroisoquinoline; or
1-amino-3-(4-pyridyl)-3,4-dihydroisoquinoline; or
1-amino-3-cyclopropyl-3,4-dihydroisoquinoline; or
1-amino-3-(2-(dimethylamino)methyl)phenyl-3,4-dihydroisoquinoline; or
1-amino-3-(3-(dimethylamino)methyl)phenyl-3,4-dihydroisoquinoline; or
1-amino-3-(2-benzothiazolyl)-3,4-dihydroisoquinoline; or
1-amino-8-chloro-3-(4-fluorophenyl)-3,4-dihydroisoquinoline; or
1-amino-3-(phenylethynyl)-3,4-dihydroisoquinoline; or
1-amino-8-methyl-3-phenyl-3,4-dihydroisoquinoline; or
1-amino-5-fluoro-3-(4-fluorophenyl)-3,4-dihydroisoquinoline; or
1-amino-8-fluoro-3-(4-fluorophenyl)-3,4-dihydroisoquinoline; or
1-amino-5,8-difluoro-3-(4-fluorophenyl)-3,4-dihydroisoquinoline; or
1-amino-6-fluoro-3-(4-fluorophenyl)-3,4-dihydroisoquinoline; or
1-amino-7-fluoro-3-(4-fluorophenyl)-3,4-dihydroisoquinoline; or
1-amino-3-ethynyl-3,4-dihydroisoquinoline; or 1-amino-3-(4-(3-aminopropyloxy)phenyl)-3,4-dihydroisoquinoline; or
1-amino-3-(3-(2-aminoethyl)phenyl)-3,4-dihydroisoquinoline; or
1-amino-3-(4-(2-aminoethyl) phenyl)-3,4-dihydroisoquinoline; or
1-amino-3-(3-(3-aminopropyl)phenyl)-3,4-dihydroisoquinoline; or
1-amino-3-(2-thiazolyl)-3,4-dihydroisoquinoline; or
1-amino-3-(2-imidazolyl)-3,4-dihydroisoquinoline; or
1-amino-3-(4-piperidyl)-3,4-dihydroisoquinoline; or
1-amino-3-methyl-3,4-dihydroisoquinoline; or
1-amino-3-(4-hydroxyphenyl)-3,4-dihydroisoquinoline; or
7-amino-5-phenyl-4,5-dihydrothieno[2,3-c]pyridine; or
7-amino-5-(3-pyridyl)-4,5-dihydrothieno[2,3-c]pyridine; or
7-amino-5-cyclopropyl-4,5-dihydrothieno[2,3-c]pyridine; or
7-amino-5-(3-furyl)-4,5-dihydrothieno[2,3-c]pyridine; or
7-amino-5-(2-furyl)-4,5-dihydrothieno[2,3-c]pyridine; or
7-amino-5-(2-thienyl)-4,5-dihydrothieno[2,3-c]pyridine; or
7-amino-5-(1-benzyl-2-pyrrolyl)-4,5-dihydrothieno[2,3-c]pyridine; or
7-amino-5-(1-methyl-2-pyrrolyl)-4,5-dihydrothieno[2,3-c]pyridine; or
7-amino-5-ethynyl-4,5-dihydrothieno[2,3-c]pyridine; or
7-amino-5-propynyl-4,5-dihydrothieno[2,3-c]pyridine; or
7-amino-5-(2-thiazolyl-4,5-dihydrothieno[2,3-c]pyridine; or
7-amino-5-(3,3-dimethylbutynyl)-4,5-dihydrothieno[2,3-c]pyridine; or
7-amino-5-(phenylethynyl)-4,5-dihydrothieno[2,3-c]pyridine; or
7-amino-5-(cyclobutyl)4,5-dihydrothieno[2,3-c]pyridine; or
7-amino-5-ethynyl-2-methyl-4,5-dihydrothieno[2,3-c]pyridine; or
7-amino-5-ethyl-4,5-dihydrothieno[2,3-c]pyridine; or
7-amino-5-propyl-4,5-dihydrothieno[2,3-c]pyridine; or
4-amino-6-phenyl-6,7-dihydrothieno[3,2-c]pyridine; or
4-amino-6-ethynyl-6,7-dihydrothieno[3,2-c]pyridine; or
4-amino-6-cyclopropyl-6,7-dihydrothieno[3,2-c]pyridine; or
7-amino-4,5-dihydrothieno[2,3-c]pyridine; or
4-amino -6,7-dihydrothieno[3,2-c]pyridine;
or a pharmaceutically acceptable salt, enantiomer or tautomer thereof.

9. The method of claim 5, wherein the disease is asthma.

10. A process for the preparation of the compound of claim 1, or a pharmaceutically acceptable salt, enantiomer or tautomer thereof, which process comprises:

(a) hydrolysis and/or deprotection of a compound of formula II or a protected derivative thereof, or hydrolysis and/or deprotection of a pharmaceutically acceptable salt, enantiomer or tautomer of a compound of formula II or said protected derivative, wherein formula II is

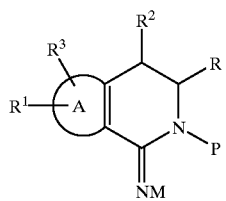

II

A, R, $R^1$, $R^2$ and $R^3$ being as defined in claim 1, P representing a protecting group and M representing an alkaline metal; or (b) deprotection of a compound of formula IIIa or IIIb or of a pharmaceutically acceptable salt, enantiomer or tautomer thereof

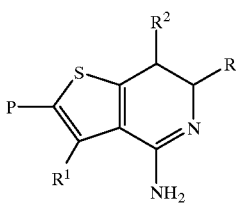

IIIa

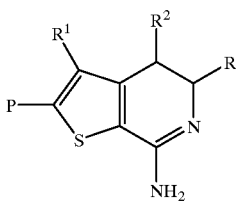

IIIb wherein R, R$^1$ and R$^2$ are as defined claim 1 and P represents a protecting group; or (c) treating a compound of formula IV or a pharmaceutically acceptable salt, enantiomer or tautomer thereof with ammonia, wherein formula IV is

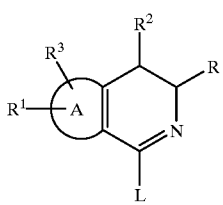

IV wherein A, R, R$^1$, R$^2$ and R$^3$ are as defined claim 1 and L is a leaving group; or (d) preparation of a compound of formula I in which R represents ethynyl, or of a pharmaceutically acceptable salt, enantiomer or tautomer of such a compound, by hydrolysis of a corresponding compound in which R represents trimethylsilylethynyl; or (e) reaction of a compound of formula V or a pharmaceutically acceptable salt, enantiomer or tautomer thereof, wherein formula V is

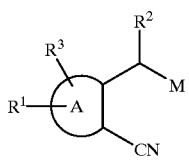

V wherein A, R$^1$, R$^2$ and R$^3$ are as defined claim 1 and M represents an alkaline metal, with a compound of formula VI or a pharmaceutically acceptable salt, enantiomer or tautomer thereof, wherein formula VI is

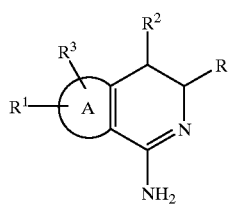

VI wherein R is as defined claim 1; or (f) preparation of a compound or a pharmaceutically acceptable salt, enantiomer or tautomer thereof, wherein the compound is of formula I in which R represents alkyl C1 to 8 substituted by a group —(CH$_2$)$_p$NR$^4$R$^5$ and one or both of R$^4$ and R$^5$ represents alkyl C1 to 6, by alkylating a corresponding compound in which one or more of R$^4$ and R$^5$ represents hydrogen; or (g) preparation of a compound or a pharmaceutically acceptable salt, enantiomer or tautomer thereof, wherein the compound is of formula I in which R represents phenyl or a six membered heterocyclic aromatic ring, the phenyl or heterocyclic aromatic ring being substituted by a group —Q(CH$_2$)$_p$NR$^4$R$^5$ and one or both of R$^4$ and R$^5$ represents alkyl C1 to 6, by alkylating a corresponding compound in which one or more of R$^4$ and R$^5$ represents hydrogen; or (h) deprotection of a compound of formula I, or a pharmaceutically acceptable salt, enantiomer or tautomer thereof, in which one or both nitrogen atoms and/or another atom is protected; or (i) preparation of a compound or a pharmaceutically acceptable salt, enantiomer or tautomer thereof, wherein the compound is of formula I in which R represents phenyl or a six membered heterocyclic aromatic ring substituted by a group —Q(CH$_2$)$_p$NH$_2$, by reduction of the corresponding azide; or (j) preparation of a compound or a pharmaceutically acceptable salt, enantiomer or tautomer thereof, wherein the compound is of formula I in which R represents piperidyl, by reduction of a corresponding compound in which R represents pyridyl.

11. A method of relieving pain in a patient, comprising administering a compound according to claim 4, or a pharmaceutically acceptable salt, enantiomer or tautomer thereof, to the patient.

12. A pharmaceutical composition comprising a compound of formula I

I wherein:
R represents
(i) phenyl, benzothiazolyl or a six membered heterocyclic aromatic ring containing 1 to 3 nitrogen atoms, which phenyl, benzo ring of the benzothiazolyl or heterocyclic aromatic ring is optionally substituted by alkyl C1 to 6, alkoxy C1 to 6, halogen, hydroxy, thioalkyl C1 to 6, benzyloxy, or a group —Q(CH$_2$)$_p$NR$^4$R$^5$; or (ii) alkyl C1 to 8, cycloalkyl C3 to 8, alkynyl C2 to 8, piperidyl, phenylalkyl C7 to 14, which alkyl, cycloalkyl, alkynyl, or piperidyl is optionally substituted by a group —(CH$_2$)$_p$NR$^4$R$^5$, the phenylalkyl being optionally substituted by a group —(CH$_2$)$_p$NR$^4$R$^5$, alkyl C1 to 6, alkoxy C1 to 6, halogen or nitro; or (iii) a 5 membered heterocyclic aromatic ring containing 1 to 3 heteroatoms selected from O, N or S, optionally substituted by alkyl C1 to 6, phenylalkyl C7 to 14 or halogen; or (iv) hydrogen or phenylalkynyl C7 to 14;

Q represents O, NR$^6$ or a bond;

R$^1$ represents hydrogen, alkyl C1 to 6, alkoxy C1 to 6, trimethylsilyl or halogen;

R$^2$ represents hydrogen, alkyl C1 to 6 or phenyl optionally substituted by alkyl C1 to 6, alkoxy C1 to 6, halogen or hydroxy;

R$^3$ represents hydrogen or halogen;

R$^4$, R$^5$ and R$^6$ independently represent hydrogen or alkyl C1 to 6, or

—NR$^4$R$^5$ together represents piperidyl, pyrrolidinyl or morpholinyl;

p represents an integer 1 to 5; and

A represents a thieno or benzo ring;

provided that when A represents a benzo ring and Q represents O, p does not represent 1;

or a pharmaceutically acceptable salt, enantiomer or tautomer thereof, in admixture with a pharmaceutically acceptable adjuvant, diluent or carrier; provided that the hydroiodide salt of the compound of formula I in which A represents a benzo ring and each of R, R$^1$, R$^2$ and R$^3$ represents hydrogen is disclaimed.

13. The method of claim 5 wherein the disease is osteoarthritis.

14. The method of claim 5 wherein the disease is rheumatoid arthritis.

15. A method of treating, or reducing the risk of, a disease or condition in which the synthesis or oversynthesis of nitric oxide forms a contributory part which comprises administering to a person suffering from or susceptible to such a disease or condition, a therapeutically effective amount of a compound of formula (I)

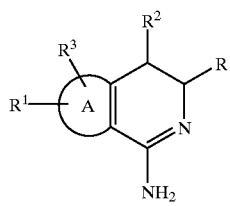

wherein:

R represents (i) phenyl, benzothiazolyl or a six membered heterocyclic aromatic ring containing 1 to 3 nitrogen atoms, which phenyl, benzo ring of the benzothiazolyl or heterocyclic aromatic ring is optionally substituted by alkyl C1 to 6, alkoxy C1 to 6, halogen, hydroxy, thioalkyl C1 to 6, benzyloxy, or a group —Q(CH$_2$)$_p$NR$^4$R$^5$; or (ii) alkyl C1 to 8, cycloalkyl C3 to 8, alkynyl C2 to 8, piperidyl, phenylalkyl C7 to 14, which alkyl, cycloalkyl, alkynyl, or piperidyl is optionally substituted by a group —(CH$_2$)$_p$NR$^4$R$^5$, the phenylalkyl being optionally substituted by a group —(CH$_2$)$_p$NR$^4$R$^5$, alkyl C1 to 6, alkoxy C1 to 6, halogen or nitro; or (iii) a 5 membered heterocyclic aromatic ring containing 1 to 3 heteroatoms selected from O, N or S, optionally substituted by alkyl C1 to 6, phenylalkyl C7 to 12 or halogen; or (iv) hydrogen or phenylalkynyl C7 to 12;

Q represents O, NR$^6$ or a bond;

R$^1$ represents hydrogen, alkyl C1 to 6, alkoxy C1 to 6, trimethylsilyl or halogen;

R$^2$ represents hydrogen, alkyl C1 to 6 or phenyl optionally substituted by alkyl C1 to 6, alkoxy C1 to 6, halogen or hydroxy;

R$^3$ represents hydrogen or halogen;

R$^4$, R$^5$ and R$^6$ independently represent hydrogen or alkyl C1 to 6, or —NR$^4$R$^5$ together represents piperidyl, pyrrolidinyl or morpholinyl;

p represents an integer 1 to 5; and

A represents a thieno or benzo ring;

provided that when A represents a benzo ring and Q represents O, p does not represent 1;

or a pharmaceutically acceptable salt, enantiomer or tautomer thereof.

16. The method of claim 15 wherein the condition is pain.

* * * * *